US008298226B2

(12) United States Patent
Hosier

(10) Patent No.: US 8,298,226 B2
(45) Date of Patent: Oct. 30, 2012

(54) ELECTROSURGICAL GENERATOR AND SYSTEM

(75) Inventor: John Roland Hosier, Cardiff (GB)

(73) Assignee: Gyrus Medical Limited, Cardiff (GB)

( * ) Notice: Subject to any disclaimer, the term of this patent is extended or adjusted under 35 U.S.C. 154(b) by 504 days.

(21) Appl. No.: 12/591,413

(22) Filed: Nov. 18, 2009

(65) Prior Publication Data
US 2010/0137854 A1 Jun. 3, 2010

Related U.S. Application Data

(63) Continuation-in-part of application No. 12/453,698, filed on May 19, 2009.

(60) Provisional application No. 61/136,109, filed on Aug. 12, 2008.

(30) Foreign Application Priority Data

May 23, 2008 (GB) .................................. 0809461.7

(51) Int. Cl.
A61B 18/12 (2006.01)
(52) U.S. Cl. ............................................. 606/37; 606/51
(58) Field of Classification Search .................... 606/34, 606/37, 41, 51, 52
See application file for complete search history.

(56) References Cited

U.S. PATENT DOCUMENTS

| 3,885,569 | A | 5/1975 | Judson |
| 4,085,603 | A | 4/1978 | Vanek |
| 4,532,924 | A | 8/1985 | Auth |
| 4,572,190 | A | 2/1986 | Azam et al. |
| 5,383,917 | A | 1/1995 | Desai |
| 6,054,914 | A | 4/2000 | Abel |
| 6,269,009 | B1 | 7/2001 | Walton |
| 6,416,509 | B1 | 7/2002 | Goble et al. |
| 6,966,907 | B2 | 11/2005 | Goble |
| 2003/0163124 | A1 | 8/2003 | Goble |
| 2003/0199868 | A1 | 10/2003 | Desai et al. |
| 2004/0032315 | A1 | 2/2004 | Illingworth |
| 2005/0171533 | A1* | 8/2005 | Latterell et al. ................. 606/48 |

(Continued)

FOREIGN PATENT DOCUMENTS

EP 0 518 565 A 12/1992

(Continued)

OTHER PUBLICATIONS

Search Report issued in U.K. Priority Application No. GB0809461.7 (Date of Search: Sep. 29, 2008).

(Continued)

Primary Examiner — Michael Peffley
Assistant Examiner — Daniel Fowler
(74) Attorney, Agent, or Firm — Nixon & Vanderhye PC

(57) ABSTRACT

An electrosurgical system has an electrosurgical generator with a multiple-phase RF output stage coupled to a multiple-electrode electrosurgical instrument. The instrument has three treatment electrodes each of which is coupled to a respective generator output driven from, for instance, a three-phase output transformer. Continuous RF output voltage waveforms are simultaneously delivered to respective generator outputs at the operating frequency, each waveform being phase-displaced with respect to the other waveforms. The magnitude of the RF output voltage waveform delivered to at least one of the generator outputs is sufficient to cause tissue vaporization at the respective treatment electrodes when the system is used for tissue treatment. Also disclosed is an electrosurgical generator in combination with a cutting forceps instrument, such that the coagulation and cutting of the tissue may be performed simultaneously.

12 Claims, 17 Drawing Sheets

U.S. PATENT DOCUMENTS

| | | |
|---|---|---|
| 2006/0015095 A1 | 1/2006 | Desinger |
| 2007/0088413 A1 | 4/2007 | Weber |

FOREIGN PATENT DOCUMENTS

| | | |
|---|---|---|
| GB | 2281863 A | 3/1995 |
| GB | 2299216 A | 9/1996 |
| GB | 2331247 A | 5/1999 |
| JP | 59 089405 A | 5/1984 |
| WO | WO 96/37156 A | 11/1996 |
| WO | WO 96/37156 A | 11/1996 |
| WO | WO 98/11938 A1 | 3/1998 |
| WO | WO 99/56647 A | 11/1999 |
| WO | WO 2006/086882 A | 8/2006 |
| WO | WO 2008/101356 A | 8/2008 |

OTHER PUBLICATIONS

Search Report issued in corresponding International Application No. PCT/GB2009/001292 (Date Search Completed: Sep. 18, 2009).

* cited by examiner

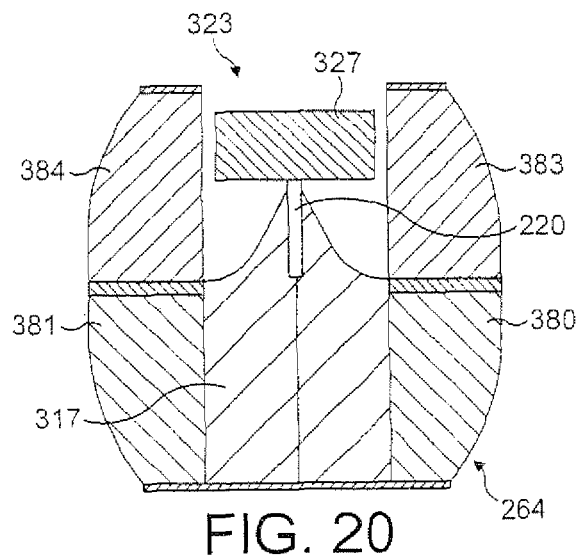
FIG. 20
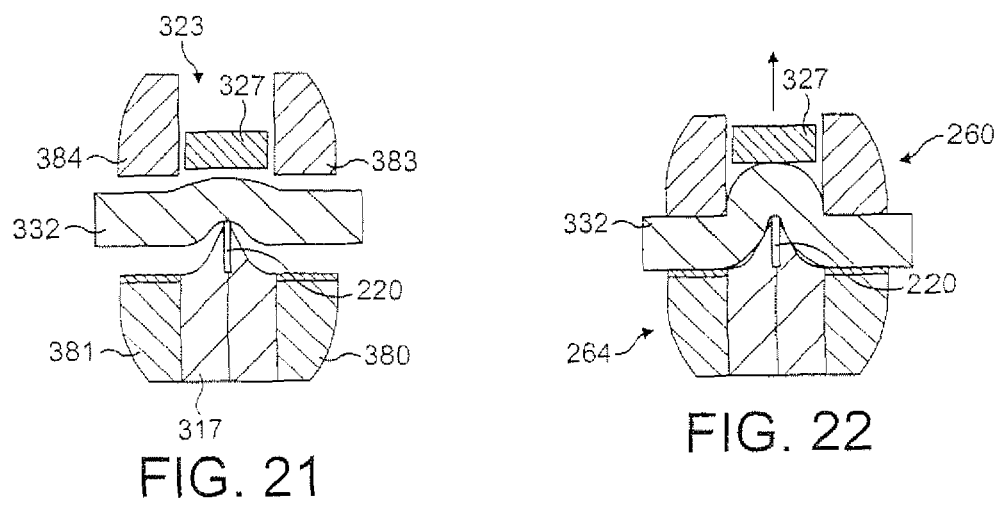
FIG. 21
FIG. 22

ELECTROSURGICAL GENERATOR AND SYSTEM

CROSS-REFERENCES TO RELATED APPLICATIONS

This application is a continuation-in-part of application Ser. No. 12/453,698, filed May 19, 2009, which claims the benefit of Provisional Application No. 61/136,109, filed Aug. 12, 2008, the entire contents of which are hereby incorporated by reference in this application.

FIELD OF INVENTION

This invention relates to an electrosurgical generator, and to an electrosurgical system comprising a generator and an electrosurgical instrument with at least three treatment electrodes. Such systems are commonly used for the cutting and/or coagulation of tissue in surgical intervention, most commonly in minimally invasive surgery as well as in laparoscopic or "open" surgery.

BACKGROUND OF THE INVENTION

Amongst known electrosurgical generators is a generator which provides different radio frequency (RF) output waveforms for tissue cutting, for tissue coagulation, and for blended cutting and coagulation, the latter being performed by rapidly alternating between a waveform suitable for cutting and a waveform suitable for coagulation. U.S. Pat. No. 6,416,509 (Goble et al) and U.S. Pat. No. 3,885,569 (Judson) disclose such generators.

WO-A-96/37156 (Issa) discloses a resectoscope having an electrode assembly with two loop electrodes. RF cut and coagulation currents are supplied simultaneously to the loop electrodes from an output transformer unit, the current passing through the patient to a grounding or return pad placed against the patient's skin.

U.S. Pat. No. 6,966,907 (Goble) teaches a generator delivering cutting and coagulating waveforms by alternating constantly between a waveform limited to a first predetermined voltage threshold value and one limited to a second, different, predetermined threshold value to form a blended signal. The disclosed system also includes means for feeding the waveform to an instrument having three or more electrodes such that a cutting RF waveform is delivered between a first pair of electrodes and a coagulating waveform is delivered between a second pair of electrodes.

SUMMARY OF THE INVENTION

The present invention provides an improved generator and system for simultaneously delivering RF output voltage waveforms across at least three outputs or instrument electrodes. In particular, according to a first aspect of the invention, an electrosurgical system comprises an electrosurgical generator for generating RF power at a generator operating frequency and an electrosurgical instrument coupled to the generator, wherein the generator comprises a multiple-phase RF output stage having at least three outputs for coupling to respective electrodes of an electrosurgical instrument for delivering RF power to the electrodes, the configuration of the output stage being such that respective RF output voltage waveforms are simultaneously delivered across each pair of the said three outputs at the operating frequency, each such waveform being phase-displaced with respect to the waveforms delivered across the respective other pairs of the three outputs, wherein the electrosurgical instrument has at least three treatment electrodes each of which is coupled to a respective one of the generator outputs for receiving RF power from the output stage of the generator, and wherein the generator is constructed and arranged such that the magnitude of the RF output voltage waveform delivered to at least one pair of the said generator outputs is sufficient to cause tissue vaporisation at the respective treatment electrodes when the system is used for tissue treatment. The phase displacement of the waveform delivered across each such respective pair of outputs with respect to the waveforms delivered across the other output pairs is typically between 10° and 170° in each case. Phase displacement of the waveform delivered across each such respective pair of outputs with respect to the waveforms delivered across the other output pairs is preferably 120° in each case.

The generator output stage may have first, second and third outputs and may be configured such that the ratio of (a) the magnitude of each of the RF output voltage waveforms delivered between the first and the second outputs and between the first and the third outputs, and (b) the magnitude of the RF output voltage waveform delivered across the second and the third outputs, is between 2 and 4. By connecting the three outputs to three respective electrodes of an electrosurgical instrument for cutting and coagulation, with the first output connected to a central cutting electrode and the second and third outputs connected to adjoining coagulation electrodes, the generator allows simultaneous cutting and coagulation, the central electrode cutting or vaporizing tissue by virtue of a high voltage cutting waveform, at least 250 volts RMS, being developed on the cutting electrode with respect to one or both coagulation electrodes, and a lower threshold voltage waveform, typically between 100 and 150 volts RMS, being developed between the coagulation electrodes.

The versatility of the generator may be increased if it has a fourth output, constituting a neutral output, the output stage being configured such that the phase displacement of the three RF output voltage waveforms delivered between (i) each of the first, second and third outputs respectively and (ii) the fourth output with respect to each other is substantially 120°.

In the preferred generator, the output stage comprises a multiple-phase output transformer, each phase having a primary winding and a secondary winding, and the phases being magnetically linked; and a drive circuit coupled to the primary windings for feeding time-varying mutually phase-displaced drive currents to the primary windings. The operating frequency is preferably between 75 kHz and 1 MHz, and typically in the region of from 200 kHz to 450 kHz. The transformer is advantageously a three-phase transformer, the secondary windings having ends forming the above-mentioned outputs of the generator. The windings of the three phases may share a common transformer core made of ferrite material, or each pair of phases may share a respective one of three annular ferrite cores. In the case of at least three phases sharing a common core, the core preferably comprises a monolithic core member having at least three limbs each carrying windings of one respective phase, the core further having an interconnecting bridge which magnetically connects the limbs. Each of the three limbs are of substantially equal cross section. In the case of a three-phase system, the monolithic ferrite core member is preferably "E"-shaped. As an alternative, the transformer core comprises three ferrite rings each carrying the windings of two phases, the windings of each phase being wound around two of the three rings.

Accordingly, the invention also provides an electrosurgical generator having a three-phase output stage with a three-phase output transformer having a ferrite core. In particular, according to a second aspect of the invention, an electrosurgical generator for generating RF power at a generator operating frequency comprises a multiple-phase RF output stage having at least three outputs for coupling to respective electrodes of an electrosurgical instrument for delivering RF power to the electrodes, the configuration of the output stage being such that respective RF output voltage waveforms are simultaneously delivered across each pair of the said three outputs at the operating frequency, each such waveform being phase-displaced with respect to the waveforms delivered across the respective other pairs of the three outputs; and wherein the output stage comprises a multiple-phase output transformer which has windings forming at least three phases and comprises a transformer core including at least one ferrite core member; and the transformer is constructed to provide at least three magnetic circuits, each magnetic circuit being inductively linked to the windings of at least two of the three phases.

In the preferred generator a drive circuit is coupled to the primary windings of the transformer and may be configured so as to synthesise phase-displaced RF waveforms directly. To do this, the drive circuit typically comprises a plurality of semiconductor switching devices coupled to a DC power supply of the generator and to the primary windings. In this case, the output stage advantageously includes, in each phase, a respective resonant circuit connected to at least one of the switching devices and the primary winding associated with that phase. In this way it is possible to smooth the switching waveforms to be more nearly sinusoidal in the primary windings and, in particular, to avoid applying third harmonic components to the three-phase transformer.

The preferred generator further comprises a control circuit connected to the switching devices, the arrangement being such that control pulses are fed to the switching devices at a predetermined repetition rate to drive them alternately to conducting and non-conducting states in a phase-displaced sequence. This causes alternating currents to be fed through the primary windings at the generator operating frequency, the current in each primary winding being correspondingly phase-displaced with respect to the currents in the other primary windings. It is by arranging for the resonant circuits to be tuned to the operating frequency that harmonics associated with the switched currents can be significantly reduced, so that the primary currents are substantially sinusoidal.

The switching devices may be arranged in pairs, each pair comprising a first transistor and a second transistor, e.g. insulated-gate bipolar transistors (IGBTs), connected in series between opposite polarity supply rails of the DC power supply and having a common connection coupled to one end of a respective primary winding. The control circuit, in this case, is configured to feed control pulses to the first and second transistors so as to drive them in opposition at the operating frequency.

The amplitude of the alternating primary currents may be varied by varying the width of the control pulses. The control circuit is preferably arranged to drive the switching devices in a 120° phase-displaced sequence.

In order to provide the higher voltage cut waveform referred to above simultaneously with a coagulation waveform, the transformer secondary windings of the preferred generator have different numbers of turns in order that the RF output voltage developed across at least one pair of the outputs is higher than that developed across another pair of the outputs.

A star-connected arrangement of transformer secondary windings is preferred in order that the generator can, if required, drive a monopolar arrangement in which a return pad is connected to the common, neutral node of the interconnected secondary windings. In this case, the secondary winding of a first phase of the transformer has a greater number of turns than each of those of the second and third phases. This means way that the RF voltage developed between the cutting electrode and at least one of the coagulating electrodes of a three-electrode instrument can be at least double that simultaneously developed between the coagulating electrodes.

As an alternative, the generator output stage has delta-connected secondary windings, the cutting electrode of the three-electrode instrument being coupled to the junction of the secondary windings of the first and second phases, and the coagulating electrodes being coupled to the junctions of the second and third phase secondary windings and of the third and first phase secondary windings respectively. In this case, each of the first and second phase secondary windings has a greater number of turns than the third phase secondary winding so that when substantially equal drive currents are fed through the primary windings, the RF voltage developed between the cutting electrode and at least one of the coagulating electrodes is greater than that simultaneously developed between the coagulating electrodes.

The three phase output can be used to drive two-electrode instruments by simply connecting the instrument electrodes to two of the phases on the secondary side, leaving the third secondary winding unconnected. Depending on the voltage output required, the switching waveforms produced by the drive circuit may be altered such that the two connected phases operate in 180° opposition (i.e. with a mutual phase displacement of)180°.

According to a further aspect of the invention, there is provided an electrosurgical generator for generating RF power at a generator operating frequency, wherein the generator comprises a multiple-phase RF output stage having at least three outputs for coupling to respective electrodes of an electrosurgical instrument for delivering RF power to the electrodes, the configuration of the output stage being such that respective RF output voltage waveforms are simultaneously delivered across each pair of the said three outputs at the operating frequency, each such waveform being phase-displaced with respect to the waveforms delivered across the respective other pairs of the three outputs, wherein the output stage comprises: a multiple-phase output transformer, each phase having a primary winding and a secondary winding, the phases being magnetically linked; and a drive circuit coupled to the primary windings for feeding time-varying mutually phase-displaced drive currents to the primary windings, and wherein the transformer core includes a monolithic ferrite core member having at least three limbs each carrying at least one winding, and an interconnecting bridge magnetically connecting the limbs, the said three limbs being of substantially equal cross-section.

According to yet another aspect of the invention, there is provided an electrosurgical generator for generating RF power at a generator operating frequency, wherein the generator comprises a multiple-phase RF output stage having at least three outputs for coupling to respective electrodes of an electrosurgical instrument for delivering RF power to the electrodes, the configuration of the output stage being such that respective RF output voltage waveforms are simultaneously delivered across each pair of the said three outputs at the operating frequency, each such waveform being phase-displaced with respect to the waveforms delivered across the respective other pairs of the three outputs; and wherein the output stage comprises a multiple-phase output transformer each phase having a primary winding and a secondary winding, the phases being magnetically linked; and a drive circuit coupled to the primary windings for feeding time-varying mutually phase-displaced drive currents to the primary windings, and wherein the transformer has a core which comprises at least three independent magnetic circuits each carrying the windings of two phases, the windings of each phase being wound around two of the three independent magnetic circuits.

According to a further aspect of the invention, an electrosurgical system comprises an electrosurgical generator for generating radio frequency (RF) power at a generator operating frequency and an electrosurgical instrument coupled to the generator, wherein the generator comprises a multiple-phase RF output stage having at least three outputs for coupling to respective electrodes of the electrosurgical instrument for delivering RF power to the electrodes, wherein the electrosurgical instrument is a forceps instrument comprising first and second jaws coupled to first and second generator outputs, the first and second jaws being adapted to coagulate tissue grasped therebetween, the forceps instrument also including a cutting electrode coupled to a third generator output, the cutting electrode being adapted to cut tissue grasped between the jaws, and wherein the configuration of the output stage of the generator is such that respective RF output voltage waveforms are simultaneously delivered across each pair of said three outputs at the operating frequency, each such waveform being phase-displaced with respect to the waveforms delivered across the respective other pairs of the three outputs, such that the forceps instrument is capable of the simultaneous coagulation and cutting of tissue.

By the term "coagulation" there is herein meant to include any method by which a previously viable tissue is rendered non-viable. This includes conventional coagulation (where the tissue is formed into an amorphous residuum, and any blood or other fluid is solidified into a gelatinous mass), and also tissue sealing or tissue welding (in which a blood vessel is closed by attaching the opposite sides of the vessel one to the other).

The generator is preferably adapted to supply an RF coagulating waveform between the first and second generator outputs, and an RF cutting waveform between the third generator output and one or both of the first and second generator outputs. In this way, tissue can be coagulated between the first and second jaws, which being cut by the cutting electrode.

According to one convenient arrangement, the cutting electrode is in the form of a longitudinally moveable blade. U.S. Pat. No. 5,445,638 describes the basic design of such a cutting forceps instrument, in which the cutting blade is purely a longitudinally moving mechanical cutting member. There are also examples of cutting forceps in which the cutting blade is longitudinally moved but is also electrically active. U.S. Pat. Nos. 6,656,177, 6,458,128 and 6,695,840 are examples of this type of device. However, in these devices the cutting blade is moved and electrically activated after the tissue has first been coagulated by signals from the generator supplied to the coagulating jaws. In the present invention, the multi-phase nature of the generator means that the cutting waveform can be delivered to the moveable blade simultaneously with the coagulating waveform being delivered to the first and second jaws.

According to an alternative arrangement, the cutting electrode is in the form of a stationary member located on one of the jaws. Once again, there are examples of instruments in which the cutting of tissue is performed by means of a stationary cutting member supplied with an electrosurgical cutting voltage. Examples include U.S. Pat. Nos. 6,174,309, 7,033,356 and 7,204,835. However, as before, the cutting blade is only electrically activated after the tissue has first been coagulated by signals from the generator supplied to the coagulating jaws. In the present invention, the multi-phase nature of the generator means that the cutting waveform can be delivered to the cutting electrode simultaneously with the coagulating waveform being delivered to the first and second jaws.

In both of these arrangements, there is no need to wait until the coagulating signal has been completely delivered to the jaws before cutting can commence. Unlike the purely sequential operation of the prior art devices, cutting can commence simultaneously with the coagulation of the tissue, leading to a quicker and more efficient procedure.

In the present invention, there is no need to wait until the coagulation signal has been completed before cutting is begun. However, it may not be appropriate in all cases to commence cutting and coagulation simultaneously. In one convenient arrangement, the generator is adapted to supply the RF output voltage waveforms in a two stage profile, with a first stage during which the generator supplies only an RF coagulating waveform to the first and second jaws, followed by a second stage during which the generator supplies an RF cutting waveform to the cutting electrode simultaneously with the RF coagulating waveform continuing to be supplied to the first and second jaws. This arrangement allows the coagulation of the tissue to be effected to a certain extent before cutting commences.

In one arrangement, the transition from the first stage to the second stage takes place after a predetermined time period has elapsed. Thus coagulation will be effected for a predetermined period of time (say 1 second) before cutting commences. Alternatively, the transition from the first stage to the second stage takes place after a measured tissue parameter reaches a predetermined threshold value. In one convenient arrangement, the measured parameter is the impedance of the tissue. In this way, the impedance of the tissue indicates that coagulation has progressed to a predetermined extent before the cutting of tissue is started. However, in both of the above arrangements, the simultaneous cutting and coagulation of tissue takes place during the second stage of the procedure, leading to a quicker and thus more effective overall process.

According to a further alternative arrangement, the generator is adapted to vary over time the magnitudes of the RF cutting voltage and the RF coagulating voltage with respect to one another. In a blended output, the relative predominance of the cutting or coagulating signals can be varied, and this can be used instead of a time delay for the cutting signal. In one convenient arrangement, the generator is adapted to change from a first stage in which the RF coagulating voltage predominates, to a second stage in which the RF cutting voltage predominates. This can either take place suddenly, at a predetermined time (such as 1 second after the initiation of the coagulation signal) or alternatively the transition from the first stage to the second stage can takes place gradually, over a certain period of time. Either way, the first and second stages ensure that cutting does not become effective before the tissue has been sufficiently coagulated, while ensuring an overlap between coagulating and cutting signals to increase the speed of the surgical process.

The invention will be described below by way of example with reference to the drawings.

BRIEF DESCRIPTION OF THE DRAWINGS

FIG. 17A is a diagram of a single-phase RF switching circuit forming part of the generator of FIG. 17;

FIGS. 20 to 25 are schematic sectional views of an alternative instrument suitable for use in the electrosurgical system of FIG. 19.

DETAILED DESCRIPTION OF THE INVENTION

Figure 1:
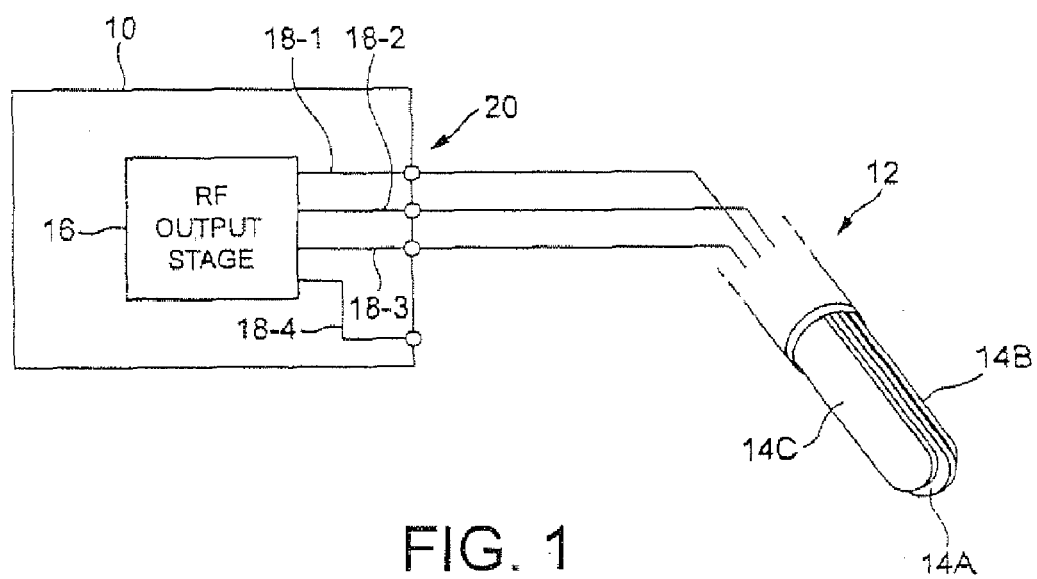
FIG. 1 is a diagram illustrating the principle of an electrosurgical system incorporating a generator in accordance with the invention.

Referring to FIG. 1, an electrosurgical system has an electrosurgical generator 10 in accordance with the invention and an electrosurgical instrument 12 having first, second, and third electrodes 14A, 14B, 14C.

The generator 10 has an RF output stage 16 with four output lines 18-1, 18-2, 18-3, 18-4 coupled to respective output connections 20 on the generator casing, to which electrosurgical instruments can be connected. In the example illustrated in FIG. 1, the electrosurgical instrument is one that operates on a bipolar principle and is shown connected to the generator 10. (Only the tip of the instrument is shown in FIG. 1.) In this instrument, the first electrode 14A is a central tissue-cutting or vaporising electrode connected to a first output line 18-1 of the RF output stage 16 when the instrument is connected to the generator 10. The second and third electrodes 14B, 14C, located on opposite sides of the cutting electrode 14A, are tissue-coagulating electrodes coupled to second and third output-lines 18-2, 18-3 of the output stage.

Tissue cutting is achieved when a relatively high RF potential is applied to the cutting electrode 14A with respect to one or both of the coagulating electrodes 14B, 14C, which act as return electrodes in this case. Generally, a voltage difference of between 250V and 400V RMS is used, preferably between 290V and 350V RMS. For tissue coagulation, a lower RF voltage is used, typically 120V RMS or less. The frequency of operation of the present generator 200 kHz, but high frequencies may be used depending on the performance of the semiconductor devices used in the generator.

The generator can be set to deliver appropriate RF cutting and coagulation voltages on its output lines 18-1, 18-2, 8-3. When the user intends the instrument to cut tissue, a cutting RF signal is applied between output line 18-1 and each of output lines 18-2 and 18-3. Conversely, when the user requires tissue coagulation, the generator is set to apply a coagulating RF waveform between output lines 18-2 and 18-3, i.e. between the coagulating electrodes 14B, 14C. It is also possible to apply different blended RF waveforms so that cutting and coagulating signals are applied to the respective electrodes simultaneously in differing proportions.

The fourth output line 18-4 of the generator allows connection of a patient return pad for monopolar operation, as is well known in the art.

Figure 2A:
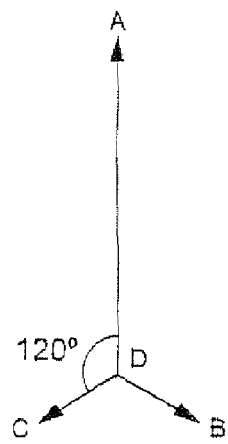
FIGS. 2A, 2B and 2C are vectoral representations of voltages developed at outputs of the generator shown in FIG. 1.

In accordance with the invention, the output stages are configured such that the respective output voltage waveforms are applied simultaneously to the three output lines 18-1 to 18-3 at a common operating frequency but phase-displaced with respect to each other, as shown by the vector diagram of FIG. 2A. Referring to FIG. 2A, the vectors DA, DB and DC are equally angularly phased-displaced with respect to each other, the angular spacing being 120°. Accordingly, the RF voltage applied to the first output line 18-1 is shown by vector DA whilst that applied to output 18-2 is shown by vector DB and is timed so as to be 120° phase-displaced with respect to the waveform represented by vector DA. Similarly, the RF voltage applied to output line 18-3, represented by vector DC, is timed so as to be 120° phase-displaced with respect to both vectors DA and DB.

Figure 2B:
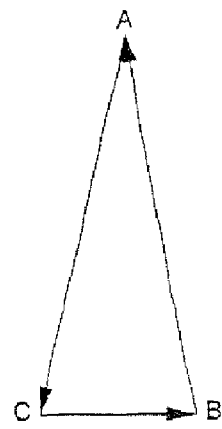

In this embodiment, the fourth output line 18-4 is connected such that it may be represented by a neutral point D in the vector diagram of FIG. 2A, this being achieved by configuring the output stage as a three-phase RF transformer with star-connected secondary windings, as already described in more detail hereinafter. It will be understood, however, that with the connections described above with reference to FIG. 1, the RF potential appearing between the electrodes 14A-14C of the instrument 12 correspond to the differences between the voltages delivered on output lines 18-1, 18-2, 18-3, as illustrated by the difference-voltage vector diagram of FIG. 2B. Specifically, in operation, a cutting potential exists between the cutting electrode 14A and a first coagulation electrode 14B, as indicated by the vector BA in FIG. 2B. Similarly, a cutting potential exists between the cutting electrode 14A and the other coagulating electrode 14C as indicated by the vector AC. A coagulating potential exists between the two coagulating electrodes 14B, 14C, as indicated by the vector CB. That the cutting voltage potentials are higher than the coagulating potential is the result of the magnitude of the RF voltage applied to the output line 18-1 with respect to the neutral point being greater than those applied to the output lines 18-2, 18-3. The way in which this is achieved is described hereinafter.

Figure 2C:
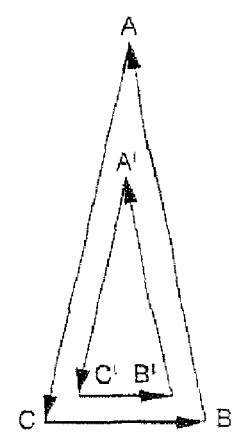

In practice, the cutting effect may be reduced by periodically reducing each of the voltages delivered on the output lines 18-1, 18-2, 18-3 to yield reduced magnitude voltage vectors B' A', A' C' and C' B', as shown in FIG. 2C. Typically, cutting is performed by applying the vector combination shown by the vectors BA, AC, CB for a period of 10 ms and the lower-voltage vector pattern B' A', A' C' and C' B' for a period of 40 ms in a 50 ms cycle. In other words, in this preferred embodiment, although the ratios between the magnitudes of the respective voltages delivered between the output terminals 18-1, 18-2, 18-3 remains the same, the output voltage differences required for tissue cutting are maintained only on a duty cycle of, in this case, 20%. For the other 80% of the 50 ms cycle, the voltage differences are sufficient only for coagulation. The duty cycle is variable depending on the degrees of cutting and coagulation required. If coagulation only is required, the generator is set to produce the lower-voltage outputs represented by the vectors B' A', A' C' and C' B'.

Figure 3:
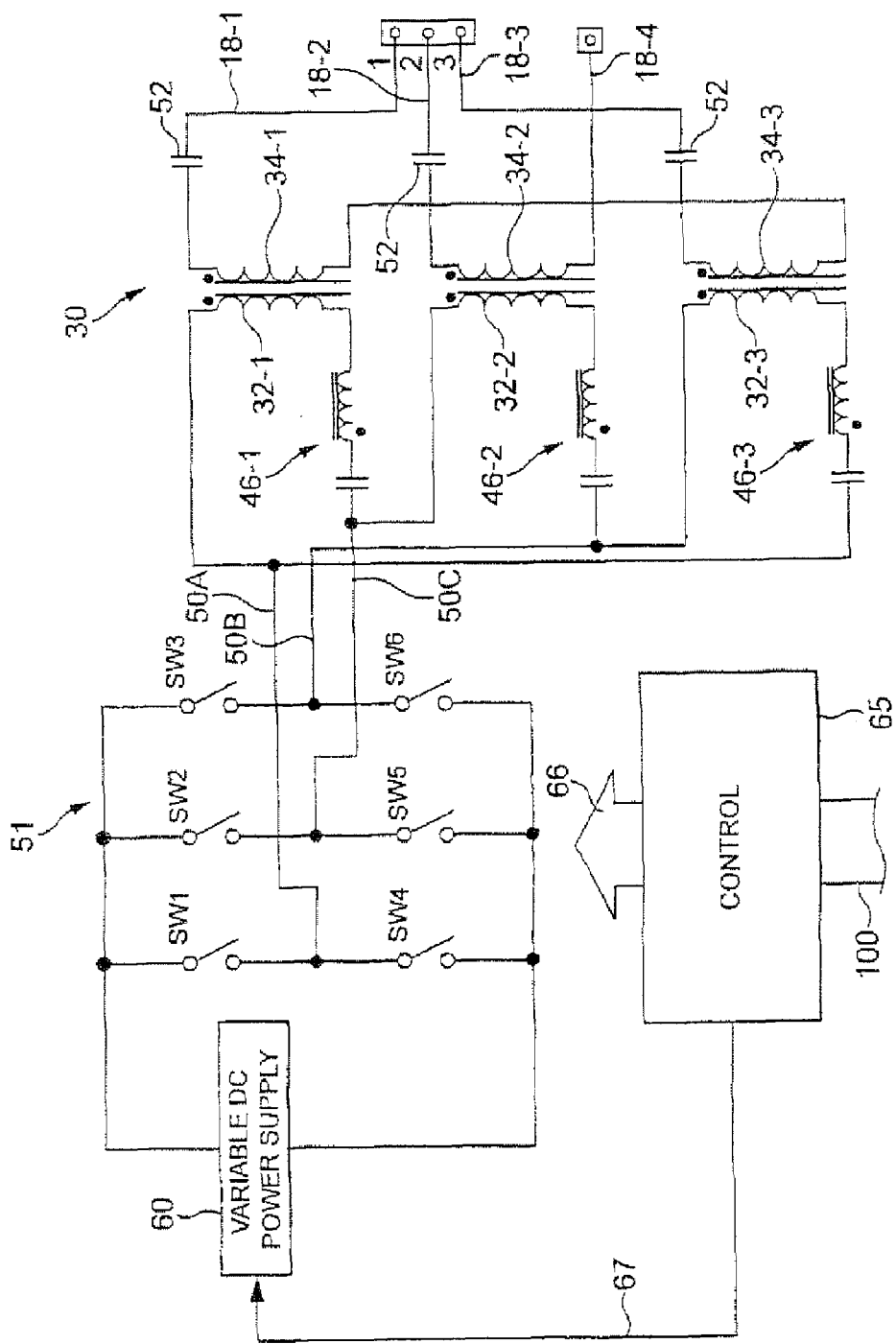
FIG. 3 is a diagram including simplified representations of the circuits of an RF output stage and a drive circuit of the generator.

Referring to FIG. 3, the RF output stage comprises a three-phase transformer 30 having first, second, and third primary-windings/secondary-winding pairs or "phases". In FIG. 3, primary and secondary windings of the first phase are shown by the reference numerals 32-1 and 34-1 respectively. Similarly, the primary and secondary winding of the second and third phases are indicated respectively by the reference numerals 32-2, 34-2 and 32-3, 34-3. It should be noted that the primary windings 32-1, 32-2, 32-3 have equal numbers of turns. However, the secondary winding 34-1 of the first phase has more turns than each of the secondary windings 34-2, 34-3 of the second and third phases, the preferred ratio of the numbers of turns being 4.3.

Figure 4:
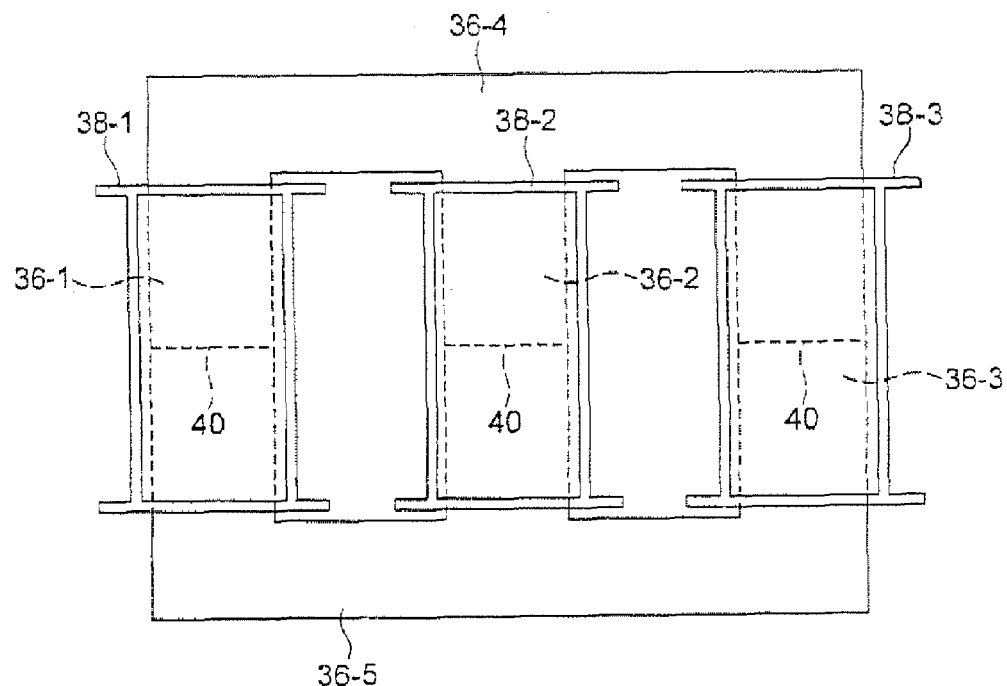
FIG. 4 is a side elevation of a three-phase transformer used in the generator.

In the preferred generator, all three pairs of primary and secondary windings 32-1, 34-1; 32-2, 34-2; 32-3, 34-3 are wound on a common transformer core. As shown in FIG. 4, each primary-secondary pair has a respective coil former 38-1, 38-2, 38-3, each former, and hence the respective primary and secondary windings, encircling a respective one of three limbs 36-1, 36-2, 36-3 of the core, the limbs being arranged in parallel and each having their ends magnetically linked by core bridge members 36-4, 36-5. In practice, the core 36 comprises two E-shaped components, each arm of each E-shaped component forming half of one of the limbs of the core and abutting one of the arms of the other E-shaped component, the abutment lines being visible as joins 40 in FIG. 4. Significantly, the limbs 36-1, 36-2, 36-3 of the core are all of equal cross sectional area and the primary-secondary pairs are matched sets. The core components are made of ferrite material, the material being selected according to the frequency of operation of the generator.

Figure 5:
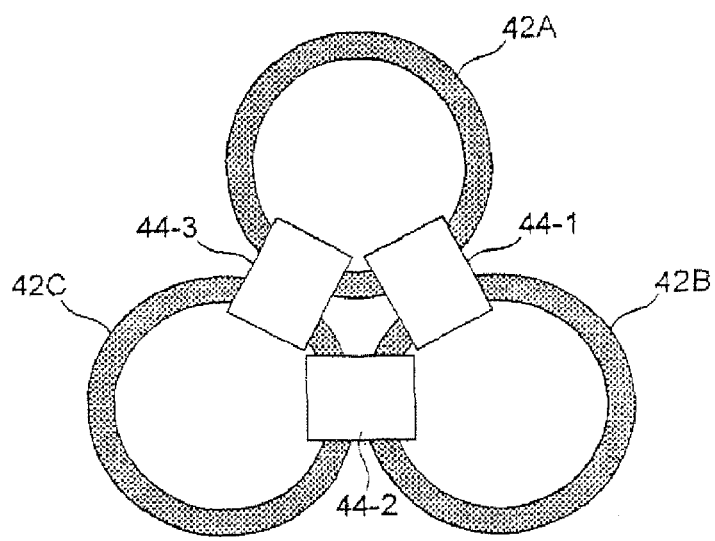
FIG. 5 is a diagram showing an alternative three-phase transformer.

With the transformer construction described above, all three core limbs are directly magnetically linked so that a magnetic flux generated in any one limb gives rise to a magnetic flux in the two other limbs. In an alternative transformer, each primary-secondary pair or "phase" shares each of two core components 42A, 42B, 42C with only a respective one of the other phases, as shown in FIG. 5. In this alternative transformer, the transformer core is made up of a plurality, here three, ferrite toroids each constituting a respective magnetic circuit. The windings of each phase 44-1, 44-2, 44-3 each links two toroids, in an equiangular triangular configuration, as shown in FIG. 5.

With both transformer constructions described above with reference to FIGS. 4 and 5, it is the transformer core arrangement that provides the magnetic circuits, the transformer core in each case providing at least three magnetic circuits.

Figure 6:
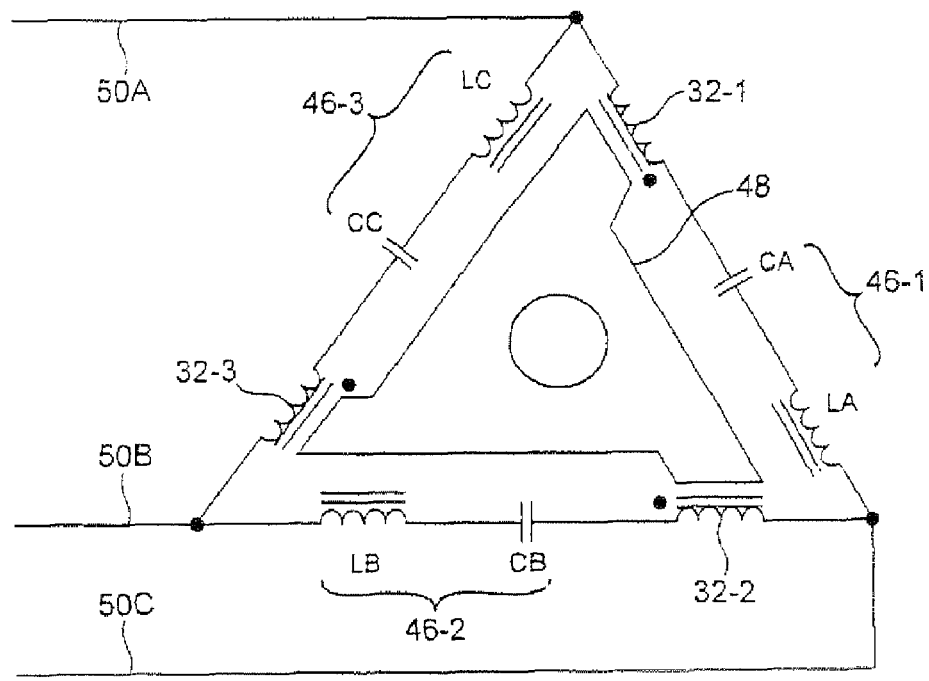
FIG. 6 is a circuit diagram of the RF output stage primary side.

Referring again to FIG. 3, the primary windings 32-1, 32-2, 32-3 are interconnected in a delta-configuration incorporating series-resonant capacitor inductor pairs 46-1, 46-2, 46-3 tuned to the generator operating frequency. This delta configuration is seen more clearly in the circuit diagram of FIG. 6, which also shows the magnetic circuit represented by the transformer core as a triangular loop 48 interconnecting the three primary windings 32-1, 32-2, 32-3. As will be seen from FIGS. 3 and 6, each side of the primary delta circuit comprises the series combination of one of the primary windings and one of the series resonant capacitor-inductor pairs. The vertices represented by the interconnections of the three sides are coupled to respective switched lines 50A, 50B, 50C, which connect the transformer 30 to a drive circuit 51.

Figure 7:
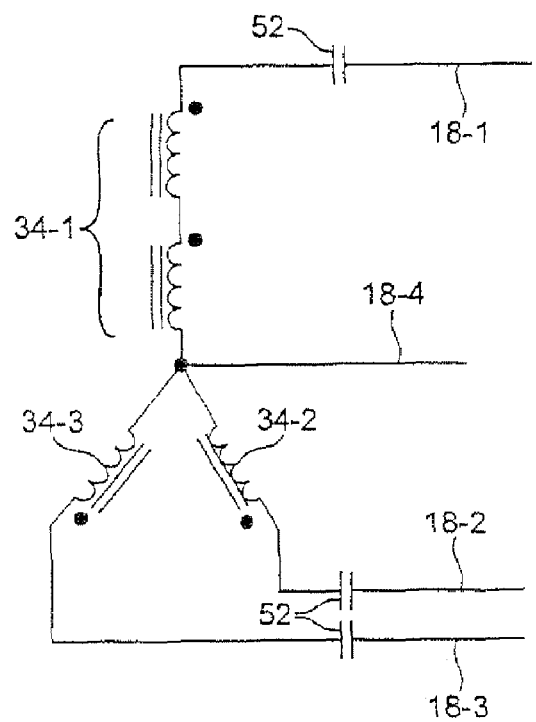
FIG. 7 is a circuit diagram of the RF output stage secondary side.

In contrast, on the secondary side, the secondary windings 34-1, 34-2, 34-3 are star-connected, as shown more clearly in FIG. 7, each primary winding being coupled to a respective output line 18-1, 18-2, 18-3 via a respective isolating capacitor 52. It will be noted that the first secondary winding 34-1 is shown as two winding sections to represent a greater number of turns of this winding compared to the second and third primary windings 34-2, 34-3. It is possible to provide a further output line from the tap between the two sections of the first primary winding 34-1 as an alternative output for multiple-electrode coagulating instruments requiring three simultaneously delivered coagulating waveforms.

RF drive waveforms for the transformer output stage are synthesised directly at the operating frequency by a bank of six switching devices arranged in pairs SW1, SW4; SW2, SW5; SW3, SW6, the two switching devices of each pair being connected in series and the pairs being connected in parallel with each other across a variable DC power supply 60. The junction between the switching devices of each pair is connected to a respective switched line 50A, 50B, 50C, as shown in FIG. 3. The switching devices SW1-SW6 are semiconductor switching devices such as bipolar or field-effect transistors (e.g. IGBTs or MOSFETs) and they form part of the drive circuit 51 for the transformer output stage, each switching devices being driven between its conducting state and its non-conducting state by control pulses from a control unit 65 of the generator. The control unit 65 controls both the switching devices SW1-SW6, via switch control lines 66, and the power supply 60, via a power supply control line 67.

The switching sequence undertaken by the bank of switching device SW1-SW6 is as shown in Table 1 below.

TABLE 1

| Steps/degrees | SW1 | SW2 | SW3 | SW4 | SW5 | SW6 |
|---|---|---|---|---|---|---|
| 1/0 | ON | OFF | ON | OFF | ON | OFF |
| 2/60 | ON | OFF | OFF | OFF | ON | ON |
| 3/120 | ON | ON | OFF | OFF | OFF | ON |
| 4/180 | OFF | ON | OFF | ON | OFF | ON |
| 5/240 | OFF | ON | ON | ON | OFF | OFF |
| 6/300 | OFF | OFF | ON | ON | ON | OFF |
| Back to 1 | | | | | | |

Figure 8A:
FIGS. 8A to 8F are waveform diagrams indicative of control pulses for controlling electronic switches of the drive circuit and showing voltage waveforms applied to primary windings of a three-phase transformer forming part of the output stage.
Figure 8B:
Figure 8C:
Figure 8D:
Figure 8E:
Figure 8F:

The references to switching angles of 0°, 60°, 120°, 180°, 240° and 360°, in Table 1 are references to phase angles with respect to a complete cycle at the operating frequency. It will be seen that the switches of each pair are driven to their conducting and non-conducting states in opposition or antiphase. The phase displacement between each pair is 120°, as will be seen by comparing FIGS. 8A, 8B and 8C. Specifically, switch SW1 conducts between 0° and 180°, switch SW2 conducts between 120° and 300°, and switch SW3 conducts from 240°, through 360°, to 60°. When switches SW1, SW2, and SW3 are conducting, their counterparts SW4, SW5, SW6 are non-conducting and vice versa. It will be understood that, given that each primary winding 32-1, 32-2, 32-3 is connected between two respective pairs of switching devices, the current through each primary winding and series-resonant circuit combination follows a pattern according to the difference between the switching pulse sequences of the two pairs, as shown in FIGS. 8D, 8E, and 8F. The fact that the switches SW1-SW6 connect each switched line 50A-50C alternately to a positive supply rail and a negative supply rail of the power supply 60 has the effect of placing a voltage square wave on each switched line. In effect, therefore, square waves are incident across each resonant circuit 46-1, 46-2, 46-3. The effect of these resonant circuits is to transform the square switching waveform substantially to a sinusoidal one at each transformer primary winding 32-1, 32-2, 32-3.

As described above, the primary windings of the transformer 30 are arranged in delta configuration and the secondary windings are arranged in star configuration. In practice, either delta or star configuration can be used for either the primary circuit or the secondary circuit, although the star-connected secondary configuration has the advantage of providing a neutral point for monopolar electrosurgical systems. In either case, it is possible to arrange for an RF voltage of greater magnitude at one output compared with the other outputs for simultaneous tissue cutting and coagulation.

Two phase energisation of the transformer, i.e. without simultaneous cut and coagulation outputs, may be achieved by driving two of the phases of the transformer 30 with a phase shift of 180° with respect to each other, the third phase being left open circuit. Such two-phase energisation is still possible with a delta-connected secondary by driving the ends of the third winding with the same signal, effectively putting a "shorted turn" on the transformer if left connected. Such a two-phase system may be used with a bipolar instrument having two electrodes or a resistive cutting loop as will be described below with reference to FIGS. 14, 15 and 16.

Figure 9:
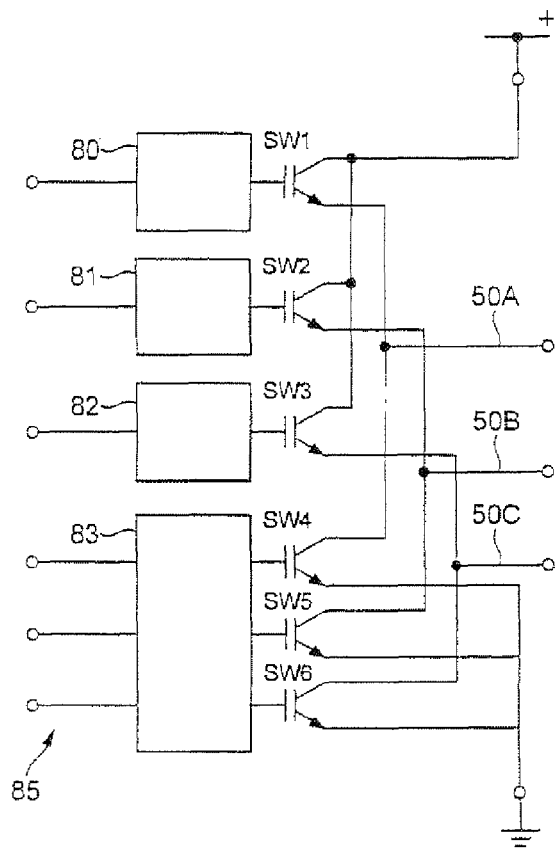
FIG. 9 is a simplified circuit diagram of the drive circuit.

In the preferred generator, the drive circuit consists of an integrated circuit power module such as the FSAM10SH60 available from Fairchild Semiconductor Corporation. FIG. 9 is a simplified circuit diagram of the module. The module has three high-voltage side switching devices SW1, SW2, SW3 in the form of IGBTs and three low-voltage side switching devices SW4, SW5, SW6, also IGBTs, the IGBTs being arranged in pairs to provide three switched lines 50A, 50B, 50C, as described above. Each IGBT is driven by an integrated circuit within the module. Specifically, the high-voltage side IGBTs SW1, SW2, SW3 are driven by respective high-voltage ICs 80, 81, 82, while the low-voltage side IGBTs are drive from a signal low-voltage IC 83. The ICs 80-83 have six signal inputs 85, one for each IGBT, allowing individual control of the IGBTs using control pulses from the control stage 65 over control lines 66 (see FIG. 3).

Figure 10:
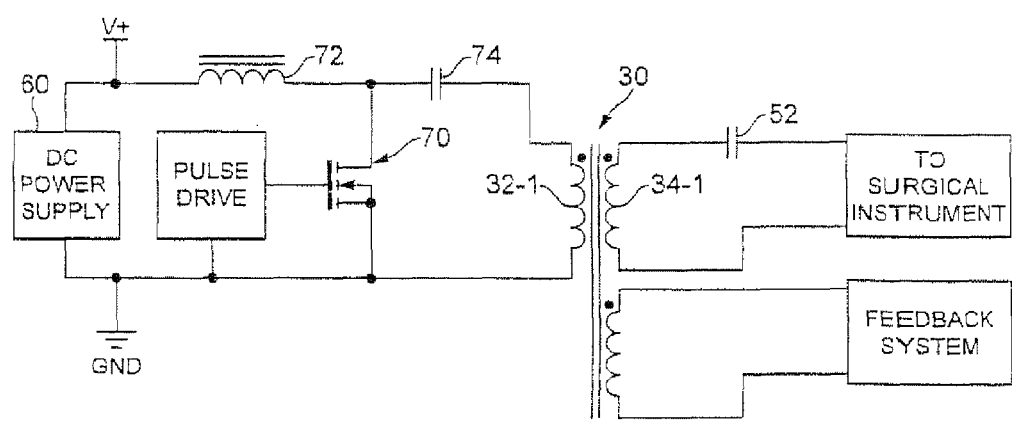
FIG. 10 is a simplified circuit diagram of one phase of an alternative drive circuit.

With regard to the drive circuit switching devices, as an alternative to paired switching devices, the switched lines may be driven by three semiconducting switching devices, i.e. one device per phase. Referring to FIG. 10 (which shows only one of three phases), in each phase a single MOSFET 70 drives a parallel-resonant network comprising an inductor 72 and a capacitor 74 into resonance at their resonant frequency (which is the operating frequency of the generator). The resulting alternating signal is applied to the respective primary winding 32-1 of the output stage transformer 30. The same configuration is reproduced in the second and third phases, switching of the three MOSFETs being phased-displaced to produce a three-phase output as described above with reference to FIGS. 3 and 8A to 8F.

Figure 11:
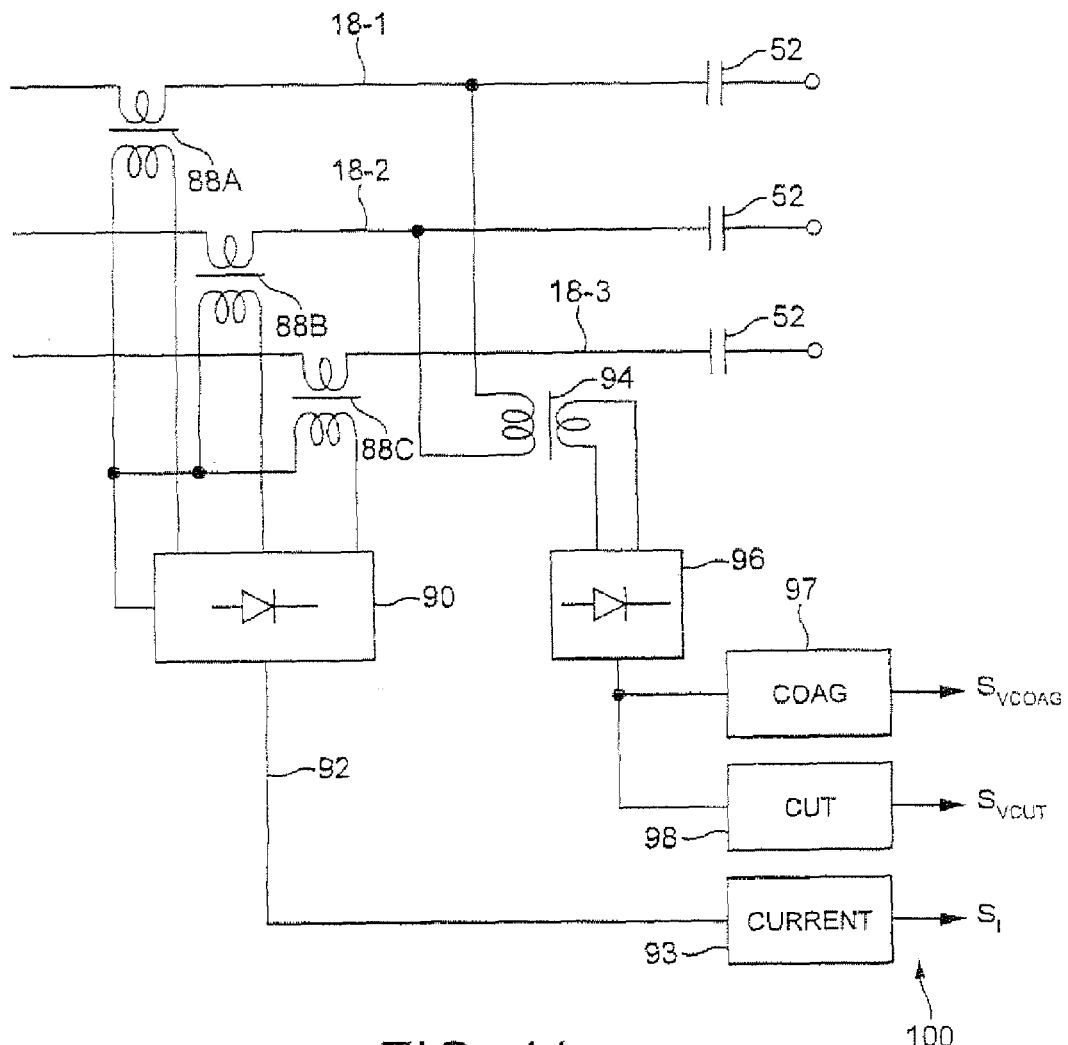
FIG. 11 is a simplified circuit diagram of a feedback stage of the generator.

The output of the generator is monitored to set current and voltage limits. Referring to FIG. 11, currents are monitored in each phase using toroidal current transformers 88A, 88B, 88C each having a primary winding connected in series in a respective output line 89-1, 89-2, 89-3. The secondary windings of the toroidal current transformers 88A-88C are coupled to rectifier circuitry 90 which includes output diodes so that the voltage obtained at the output 82 of the rectifier circuitry represents the highest of the three-phase currents in output lines 18-1, 18-2, 18-3. This current signal is applied to a first comparator 94 which produces a current sensing output $S_I$ when the current representation on line 92 exceeds a predetermined threshold representing a generator output current threshold. Only a single voltage sensing transformer 94 is used, its primary winding being coupled across two of the output lines 18-1, 18-2. As in the case of the current sensing circuits, the transformer secondary winding is coupled to a rectifier 96, the rectified output-voltage-representative signal on the rectifier output line 98 being applied to two comparators 97, 98, one setting a coagulation voltage threshold and the other setting a cut voltage threshold to produce respective coagulation voltage and cut voltage sensing signals $S_{VCOAG}$ and $S_{VCUT}$. These current and voltage sensing signals are fed back to the control stage 65 (see FIG. 3) on sensing lines 100.

The control stage 65 will now be described in more detail with reference to FIG. 12. In the preferred generator, the control stage is implemented in a CPLD (complex programmable logic device) comprising a number of "macro cell" registers which, in combination with AND/OR gates allows Boolean equations to be implemented, a compiler taking a script file or a schematic which is boolean to a sum of products. The CPLD produces control pulses for driving the switching devices SW1-SW6 (FIG. 3) to synthesise phase-displaced RF waveforms. It will be understood that such waveforms may be generated in a variety of ways, the CPLD being only one possible device.

Figure 12:
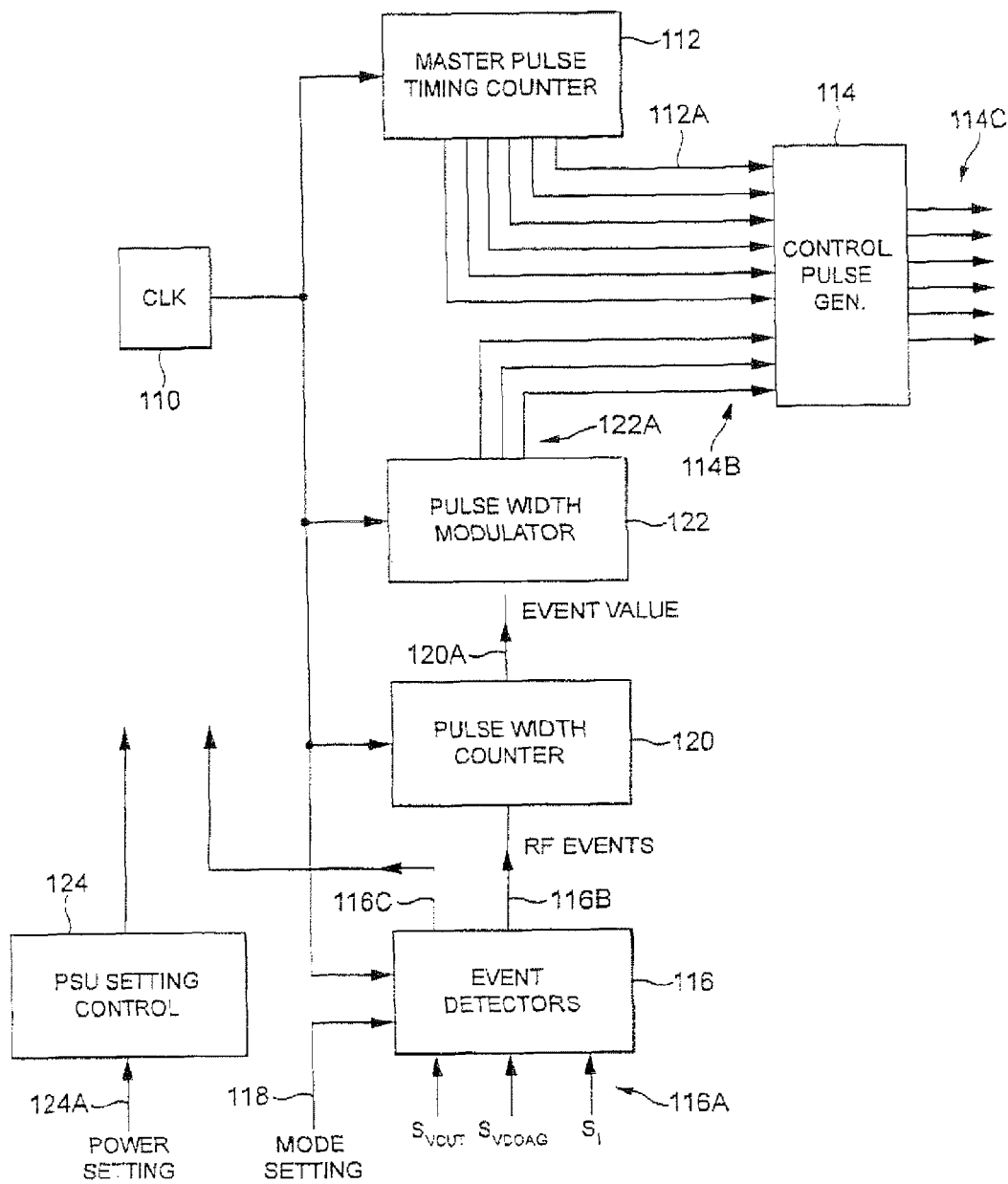
FIG. 12 is a block diagram of a control section of the generator.

Referring to FIG. 12, a number of logic blocks are implemented using the CLPD to produce the required control pulses. Several of the blocks are clocked by a 25 MHz clock 110.

In a master pulse timing counter 112, the 25 MHz clock signal is divided by 120 to yield the generator operating frequency of 208 kHz. During each RF cycle of the operating frequency, the count output counts up at 25 MHz from 0 to 120 before being reset, and six output registers are configured to be set and reset at counts corresponding to 0° and 180° for the first phase switching devices, at 120° and 300° for the second phase switching devices and at 240° and 60° for the third-phase switching devices, thereby producing six control waveforms on the master pulse timing counter outputs 112A that correspond to the three waveforms described above with reference to FIGS. 8A to 8C, and their three inverses. These register outputs are fed to a first set of six inputs of a control pulse generator 114.

Control of the generator output voltage and output current is effected by applying pulse width modulation to the control signals for the switching devices SW1-SW6 (FIG. 3) in response to the sensing signals fed back from the output current and voltage sensing circuitry described above with reference to FIG. 11. The sensing signals $S_{VCOAG}$, $S_{VCUT}$ and $S_I$ are fed to respective inputs 116A of an event detectors section 116 of the CPLD. Depending on the mode setting on line 118, the event detectors produce "RF event" signals on two event detector outputs 116B, 116C when either the cut voltage sensing signal $S_{VCUT}$ or the coagulation voltage sensing signal $S_{VCOAG}$ indicates that the cut output voltage threshold or the coagulation output voltage threshold respectively has been exceeded. RF event signals are also produced on outputs 116B, 116C if the output current threshold, as indicated by sensing signal $S_I$ indicates that the output current threshold has been exceeded.

A first RF event signal, produced on the first output 116B of the event detector circuit 116 is fed to a pulse width counter 120 configured to generate an event value signal on its output 120A which has a normal value when no RF "events" are detected and a value which deviates from the normal value by an amount depending on the length of time that the sensing signals on inputs 116A of the event detectors are indicative of a threshold having been exceeded. The event values are fed to a pulse width modulator 122 which has three outputs 122A coupled to a second set of three inputs 114B of the control pulse generator 114 that constitute blocking inputs. The pulse width modulator 122 operates to convert the event values into variable width blocking pulses that are timed so that, when combined with the basic timing sequences fed to the control pulse generator on lines 112A, the widths of the control pulses fed from the outputs 114C of the control pulse generator to the bank of switching devices SW1-SW6 (see FIG. 3) are decreased when RF events are detected.

In this connection, as described above, the switching devices of each pair of the bank of switching devices SW1-SW6 are driven in anti-phase, i.e. 180° out of phase with each other so that, in voltage terms, the junction of the two devices of each pair is alternately pulled to the voltages of the positive and negative supply rails of the power supply 60 (FIG. 3). The width of each period of conduction of each switching device is reduced by reducing the width of the control pulses as described above. The configuration of the pulse width modulator 122 and the control pulse generator 114 is such that the blocking pulses on the blocking pulse inputs 114B of the control pulse generator 114 have the effect of retarding the leading edge of each control pulse and advancing the trailing edge of each such pulse, as shown by the dotted lines in FIGS. 8A, 8B and 8C. It will be appreciated, therefore, that for each pair of switching devices SW1, SW4; SW2, SW5; SW3, SW6 there are periods when one of the devices is conducting and the other is non-conducting, periods when neither of the two devices is conducting, and periods when the other device is conducting and the first device is non-conducting. In the periods when neither device is conducting, no current is supplied from the power supply via the respective switching device pair. Accordingly, when an "event" is detected, power to all three transformer phases is reduced to a degree depending on the duration of the event, thereby reducing the output power of the generator until the output voltage or output current no longer exceeds the relevant threshold.

One of the functions of the event detector stage 116 is to synchronise the RF event signal on output 116B with the RF cycles generated by the master pulse timing counter 112 insofar as the RF event signal duration is sufficient to produce blocking pulses of the required length. The RF event may occur at any time in the RF cycle and may be of short duration compared to the RF cycle time. On such occasions the event detector stage stores the occurrence of the event and is cleared at the end of every RF cycle.

The pulse width modulation process just described allows the generator circuitry to react very rapidly to over-voltage or over-current events. Further, slower output power reduction is obtained by feeding a second RF event signal from the second output 116C of the event detector stage 116 to interrupt the power supply, causing the voltage fed to the bank of switching devices SW1-SW6 to reduce. In this case, the synchronisation of the RF event signal on the second output 116C of the event detector stage 116 is matched to the cycling time of control circuitry within the power supply. Basic power setting is achieved through a power setting control section 124 of the CPLD, which has inputs 124A responsive to control settings on a front panel of the generator. Blending of output voltage combinations, as described above with reference to FIG. 2C, may be produced by constantly alternating the mode setting input on line 118 to the event detector 116, according to a predetermined duty cycle and/or by automatically alternating the PSU setting control section 124 in order to reduce the supply voltage produced by the variable DC power supply 60 (see FIG. 3), again, according to the predetermined duty cycle.

Figure 13:
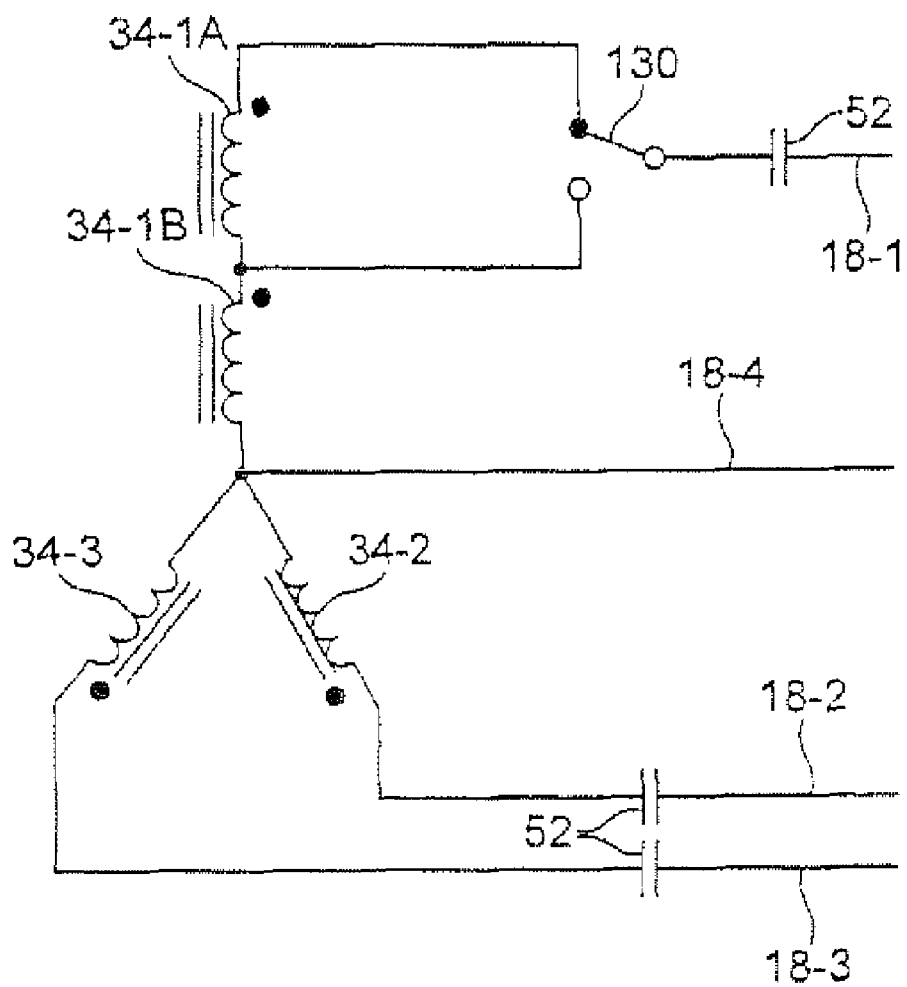
FIG. 13 is a circuit diagram showing a modified RF output stage secondary side.

As a further alternative mode of operation for pure coagulation of tissue, the first output line 18-1 of the RF output stage 16 may be coupled to the secondary winding 34-1 by a switching device, specifically a relay, wired to couple the output line 18-1 alternatively to the end of the star-connected first secondary winding 34-1 or to a tap between the two parts 34-1A, 34-1B of the winding, as shown in FIG. 13. The winding part 34-1B nearest the star point has the same number of turns as the second and third secondary windings 34-2, 34-3 so that, when the switch 130 is in a "coagulation" position, voltages appropriate for coagulation only are delivered between the three output lines 18-1, 18-2, and 18-3 (and with respect to the neutral output line 18-4, if used). In this case, the vector diagram of the RF difference voltages on output lines 18-1, 18-2 and 18-3 is in the form of an equilateral triangle, each difference voltage having a magnitude of about 120 volts RMS.

Figure 14:
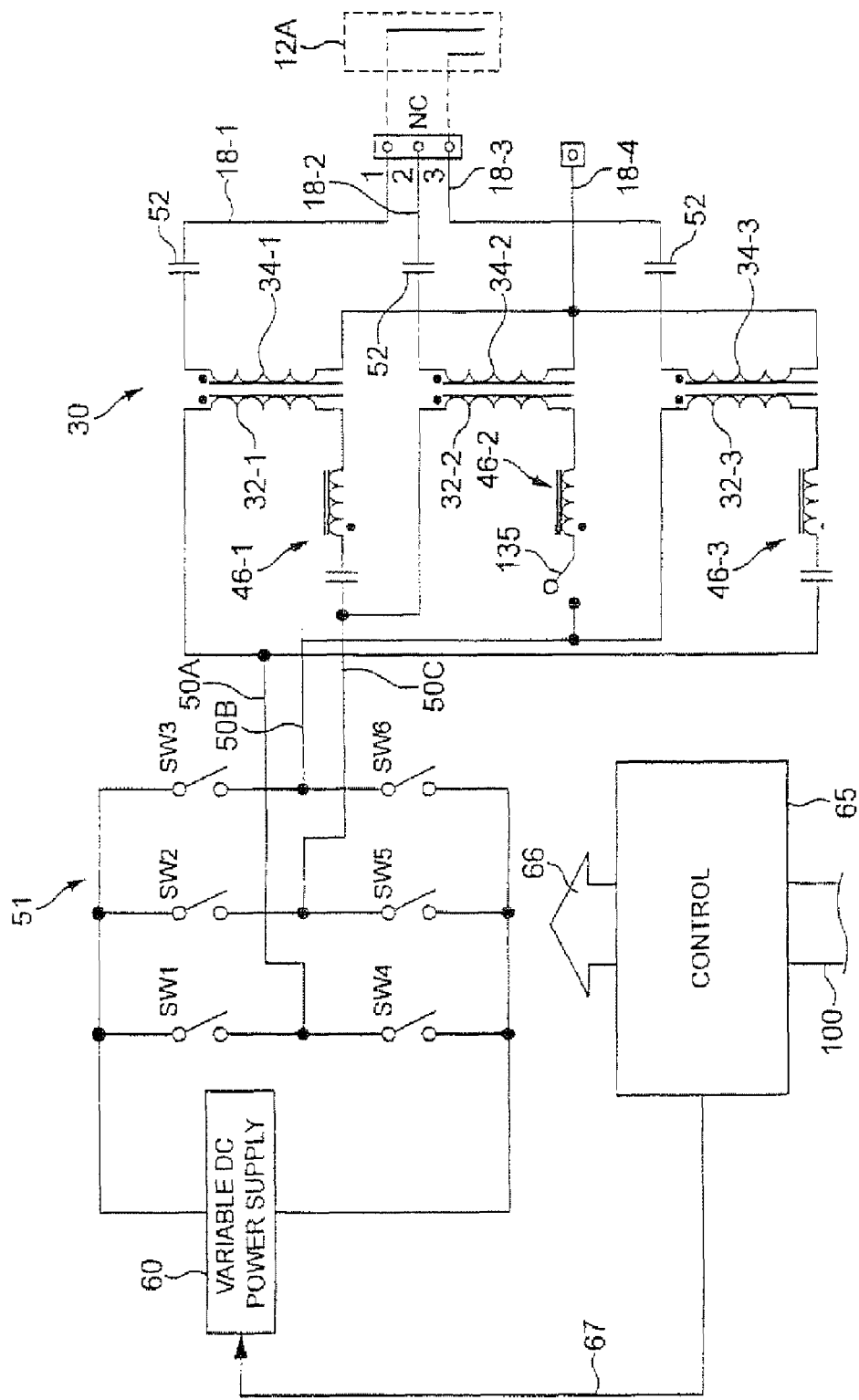
FIG. 14 is a diagram of another alternative RF output stage.

The generator may be configured to drive two-electrode instruments, as shown in FIG. 14. Only the first 34-1 and one other 34-3 of the secondary windings of the transformer 30 are connected to the instrument 12A, the remaining secondary winding 34-2 being left not connected. It is preferred that a relay 135 is incorporated in series in the second-phase primary circuit, i.e. the phase in which the secondary winding is not connected.

Figure 15:
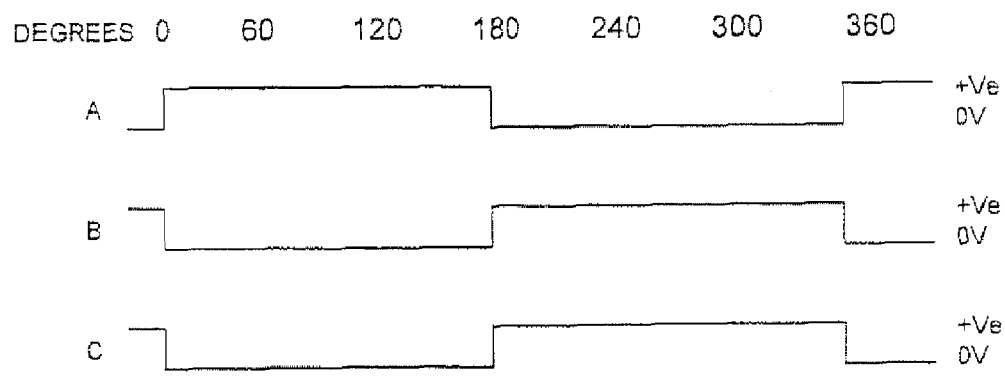
FIG. 15 is a set of three waveform diagrams illustrating control pulses for controlling electronic switches of the RF output stage of FIG. 14 when used to power a two-electrode instrument.

The waveforms driving the switching devices SW1-SW6 of the drive circuit 51 may remain as described above with reference to FIGS. 8A to 8F but, preferably, are modified such that those of the third phase (and the second phase, if desired) are driven in direct 180° antiphase with respect to the first phase, as shown in FIG. 15. It can be seen that there is a driving waveform, i.e. the difference between drive inputs A and B, across the first primary winding 32-1, whereas the third primary winding 32-3 has the same waveform across it, but inverted. The secondary primary winding has both ends at the same potential, therefore no voltage is developed across it. The flux from the other two windings are in opposition in the central limb 36-2 (FIG. 4) of the transformer core. Although this results largely in cancellation of magnetic flux components from the other limbs 36-1, 36-3, the relay 135 is included to avoid imbalances owing to small variations in the winding characteristics.

Figure 16:
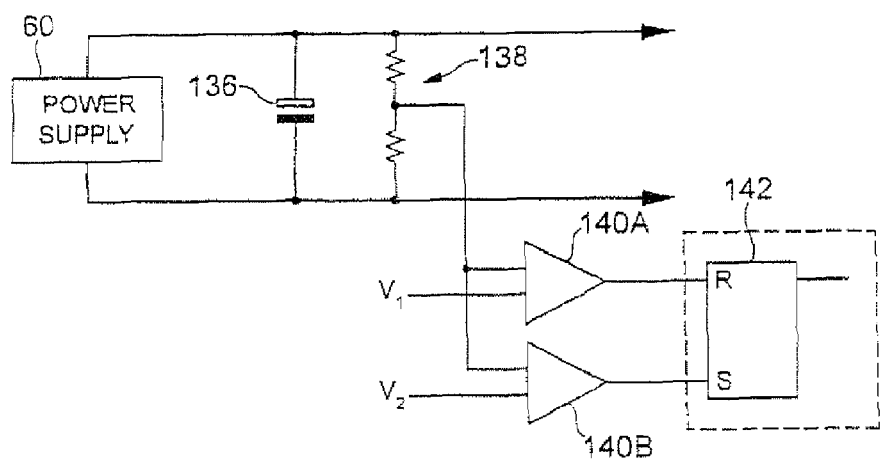
FIG. 16 is a simplified circuit diagram of a circuit for use with the RF output stage shown in FIG. 14, for driving a high power two-electrode electrosurgical instrument.

Providing for a two-electrode generator mode further increases the versatility of the generator insofar as it may be used to power a bipolar loop electrode instrument such as that disclosed in U.S. Pat. No. 7,211,081 the disclosure of which is incorporated herein by reference. Referring to FIG. 16, an energy storage capacitor or capacitors 136 is included across the supply rails of the variable DC power supply 60, together with a potential divider 138 which feeds the inputs of two comparators 140A, 140B for sensing upper and lower supply voltage thresholds using different reference voltage inputs $V_1$ and $V_2$. The comparator outputs are coupled to an RS register in the control unit 65 (FIG. 14) of the generator for enabling and disabling the generation of RF power via the drive circuit

51. In operation of the circuit of FIG. 16, the power supply 16 initially charges up the capacitor 136 until the supply voltage across the potential divider 138 reaches an upper threshold value at which the first comparator 140A changes state (typically when the supply voltage is 135 volts) whereupon the register 142 enables the RF generation process with the result that a high current (typically 12 amps) is delivered across the electrodes of the instrument 12A, which are immersed in saline at the operation site. This initial high current burst reduces the voltage on the capacitor 136 to a lower level (about 105 volts), whereupon the second comparator 140B changes state and the register 142 stops of the RF generation process. With the RF output stopped, the power supply 60 once again charges up the capacitor 136 so that the voltage increases so as to return to the point at which the first comparator 140A trips once again, causing the RF generation process to be restarted. In practice, owing to the high current level passed through the saline between the electrodes of the instrument 12A, the saline is vaporised and a plasma is produced, thereby presenting a higher impedance to the RF output stage. This, in turn, means that the voltage across the capacitor 136 and, therefore, across the drive circuit 51 is maintained at the upper threshold (135 volts) and the plasma is maintained between the instrument electrodes.

Figure 17:
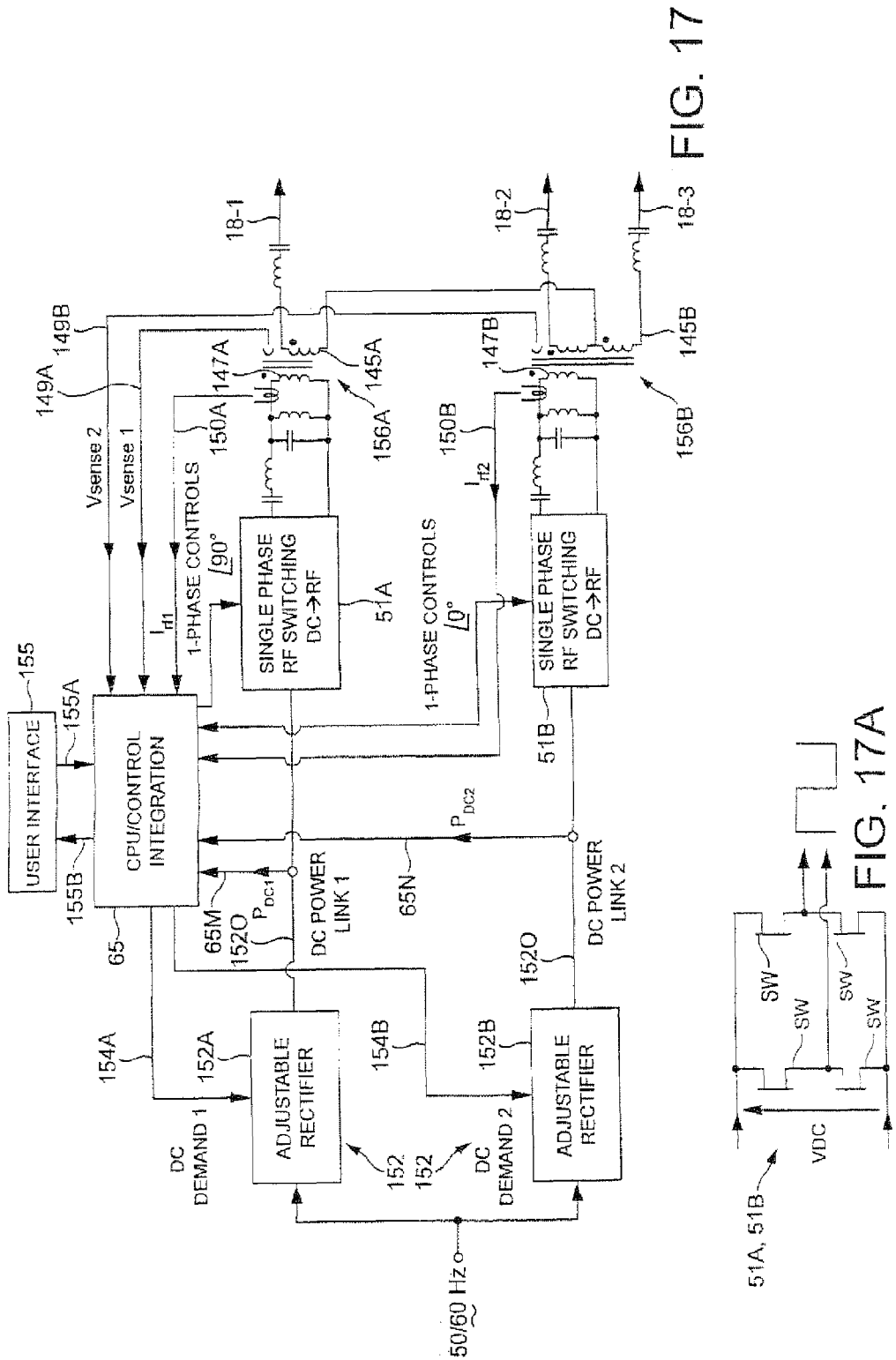
FIG. 17 is a block diagram of a further alternative generator in accordance with the invention.
Figure 18:
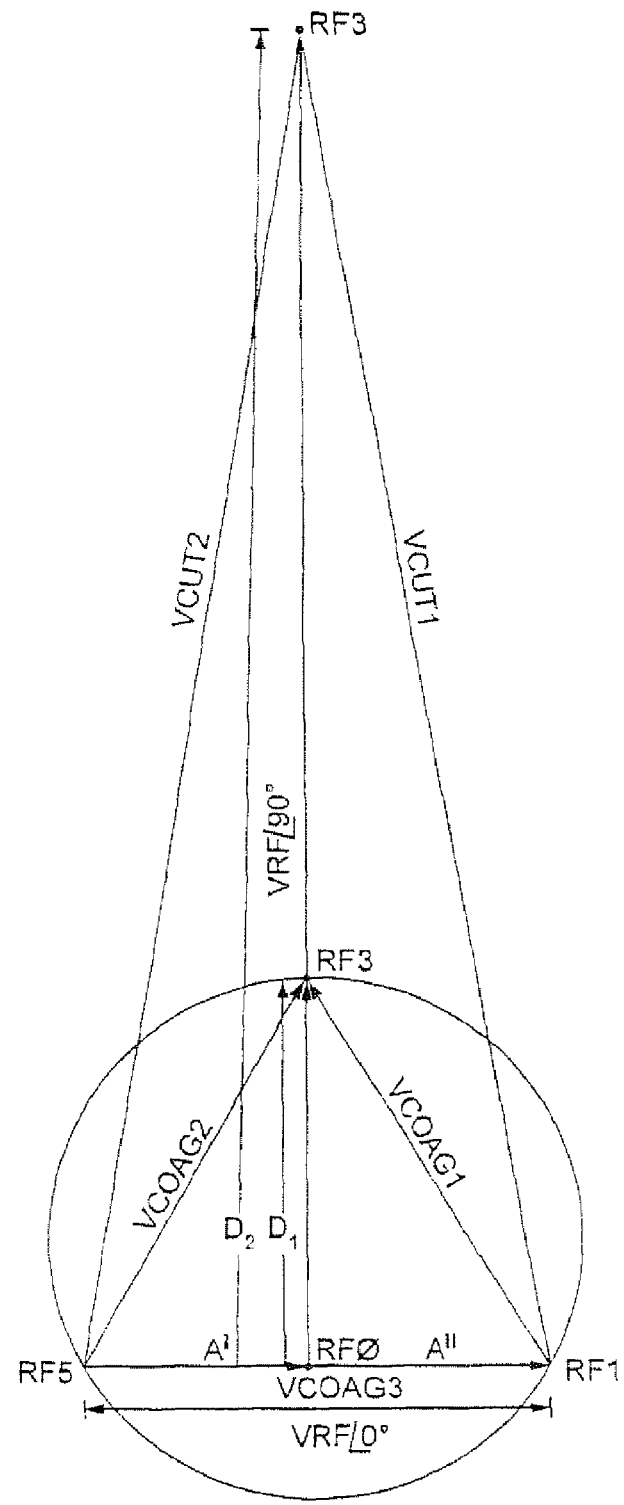
FIG. 18 is a vector diagram representing voltages developed at the outputs of the generator shown in FIG. 17.

In a further alternative generator in accordance with the invention, phase-displaced RF output voltage waveforms are produced using two single-phase output transformers driven with orthogonal drive waveforms, as shown in FIGS. 17 and 18.

Referring to FIG. 17, the configuration of the generator is similar to that described above with reference to FIGS. 3 and 9 to 12 insofar as three output lines 18-1, 18-2, 18-3 deliver RF output voltage waveforms from transformer secondary windings 145A, 145B. The output windings and interconnections of the generator of FIG. 17 are shown by way of example only. The respective transformer primary windings 147A, 147B are driven via LC filtering components by drive circuitry 51A, 51B which directly synthesises RF square-wave drive waveforms (typically having a peak-to-peak amplitude of 2V). As in the generator described above with reference to FIG. 3, the drive circuitry 51A, 51B includes semiconductor switching devices SW connected in a bridge configuration, as shown in FIG. 17A. A control unit 65 drives the switching devices SW of the switching circuitry (FIG. 17A) and pulse-width-modulates the drive signals to the switching devices in response to RF voltage and current sensing inputs 149A, 149B, 150A, 150B which, in this case, are taken from the secondary side and primary side respectively of the transformer output stage. A user interface 155 coupled to the control unit 65 allows dosage, intensity and waveform selection via control line 155A and receives treatment progression data from the control unit 65 via output line 155B. Furthermore, as in the embodiment described above with reference to FIG. 12, AC-mains-driven power supply circuitry 152A, 152B controls output power by controlling supply voltages in response to event signals from the control unit 65 via demand lines 154A, 154B. Each power supply circuit comprises an adjustable-DC-output rectifier, and DC power measurement signals picked up from the power supply circuitry outputs 152D are fed via further sensing lines 65M, 65N to the control unit 65.

The main differences between this generator and that described above with reference to FIGS. 3 and 9 to 12 are that it has a first single-phase drive circuit 51A synthesising drive signals for a first single-phase transformer 156A, the secondary winding 145A of which is coupled to a cutting output line 18-1, whereas a second, independently controlled single-phase drive circuit 51B synthesises an RF drive waveform which is orthogonal to that generated by the first drive circuit 51A, for a second single-phase transformer 156B the secondary of which has respective ends coupled to second and third output lines 18-2, 18-3 for connection to coagulation electrodes. Note that the secondary winding 145B of the second transformer 156B has a central tap 158 which is connected to the opposite end of the secondary winding 145A of the first transformer 156A from the first RF output line 18-1.

Bearing in mind that the waveforms developed across the two secondary windings 145A, 145B are phase-displaced by 90° with respect to each other, it will be appreciated that, using the tap 158 as a reference, a vectoral representation of the output voltages on the output lines 18-1, 18-2, 18-3 is in the form of a "T", as shown in FIG. 18. (In FIG. 18, the "T" appears inverted, because the voltages on the second and third output lines 18-2, 18-3 (A', A") appear at the bottom of the diagram.) The output voltages developed between the output lines 18-1, 18-2, 18-3 are phase-displaced according to a triangular vector pattern, in the same way as described above with reference to FIG. 2B.

In this embodiment, the power supply circuitry 152 consists of two separately controllable DC power supply units 152A, 152B each driving a respective drive circuit 51A, 51B. This means that the magnitude of the cutting voltage output waveform, which is the output waveform obtained from the first transformer 156A and is determined, in part, by the number of turns on its secondary winding 154A, is controllable separately from the magnitude of the coagulation voltage delivered between output lines 18-2, 18-3 via the second transformer 156B. The number of turns of the secondary winding 145B is set to produce a coagulation voltage which is much lower than the cut voltage developed between, respectively, the two output line pairs 18-1, 18-2 and 18-1, 18-3.

As will be evident from this description, alteration of the cutting voltage amplitude causes no alteration in the coagulation voltage amplitude VCOAG3 in FIG. 18. Alterations to the coagulation voltage amplitude VCOAG3 cause minor percentage changes to the relatively larger cutting voltages VCUT1 and VCUT2, and these are independently compensated for within the control circuitry by adjustment of the RF square-wave output from the first drive circuit 51A, determined by the DC voltage supplied from the first power supply unit 152A.

For multi-phase coagulation without cutting, the first drive circuit 51A, which synthesizes cutting voltage, is operated at slightly less than one third of the amplitude used for cutting in order to match the voltage amplitude synthesized by the coagulation-only drive circuit 51B. This results in three equal-amplitude RF coagulation voltages VCOAG1, VCOAG2 and VCOAG3 as shown in FIG. 18, each phase-displaced by 120° with respect to the others.

Rapid output voltage adjustment can be performed, as described above with reference to FIGS. 11 and 12, by pulse width modulation or by interrupting individual RF cycles. The generator may optionally include a local closed loop, as shown, to regulate the DC power applied to the RF switching stages.

In a further alternative generator, not shown in the drawings, a 3-phase output transformer may have star-connected primary windings. In this case, each switching device pair SW1, SW4; SW2, SW5; SW3, SW6 of the drive circuit 51 described above with reference to FIG. 3 has its respective output line 50A, 50B, 50C connected to one primary winding 32-1, 32-2, 32-3 only. A half-bridge bus capacitor leg connected in parallel with the switching device pairs has a central node coupled to the star point formed by interconnecting the other ends of the three primary windings 32-1, 32-2, 32-3. The half-bridge bus capacitor leg consists of two large capacitors connected in series across the power supply rails, each with a DC biasing resistor coupled across it in parallel, the star point being connected to the central junction of the two capacitors and the two resistors.

Figure 19:
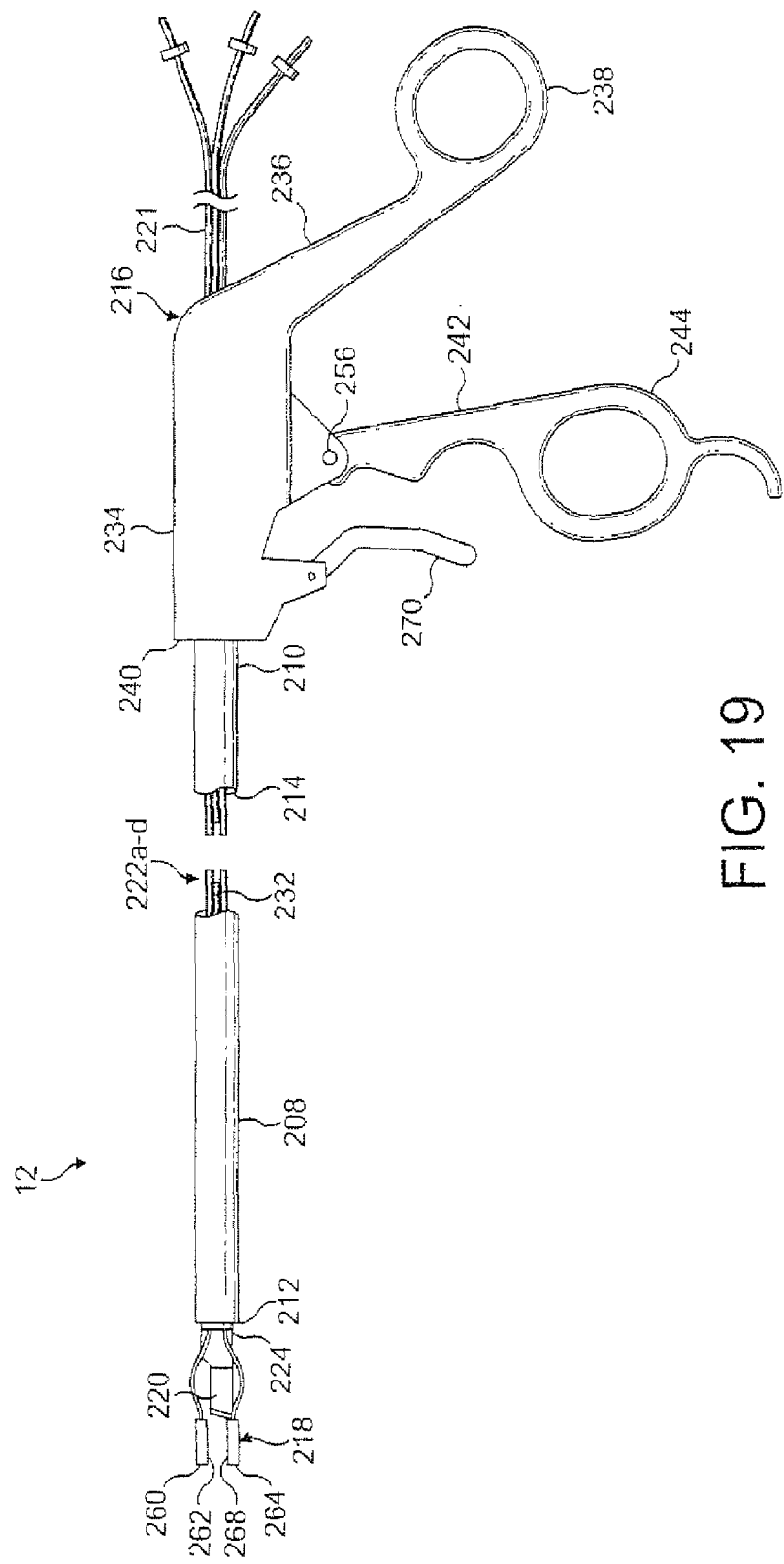
FIG. 19 is a schematic side view of an instrument suitable for use with in an electrosurgical system in accordance with an alternative aspect of the invention.

FIG. 19 shows an alternative instrument 12 that can be used in connection with the generator 10. The instrument comprises an elongated rigid tubular member 208 which may be formed from a variety of materials such as stainless steel. The outer tubular member 208 has a proximal end 210, a distal end 212 and a lumen 214 extending the entire length thereof. The outer tubular member 208 preferably has approximately an 8 mm lumen and is sized to be used within a trocar with a 10 mm inner diameter. A scissors type handle 216 is located at the proximal end of the outer tubular member 208. Coagulating forceps 218 and a conductive cutting blade 220 extend out from the distal end of the outer tubular member 208. The instrument is connected through leads 221 to the generator 10.

Located in the lumen of the outer tubular member is a plurality of wire receiving tubular members 222a-222c, which extend the entire length of the tubular member 208 in spaced apart arrangement. Passing through these wire receiving tubular members 222a-222c are the conductor wires for the coagulating forceps 218, and also for the cutting blade 220. Also extending the length of the lumen of the outer tubular member 208 is a blade actuating rod 232 to which the blade 220 is affixed. The plurality of wire receiving tubular members 222a-222c are arranged in a spaced apart fashion so that the blade actuating rod 232 can readily reciprocate within the lumen without interference from the conductor wires. A wire guide sleeve 224 is located at the distal ends of the wire receiving tubular members 222a-222c and within the distal end of the lumen of the outer tubular member 208.

The handle 216 has a stationary part made in two halves. Each half has a longitudinally extending section 234 that terminates at the handle's distal end 240. The proximal end of the handle halves form a downward sloping arm 236 that terminates in an annular finger-receiving opening 238. The proximal end of the outer tubular member 208 is frictionally fitted into the distal end 240 of the handle. A moveable arm 242 is pivotally mounted on the handle at pivot 256 and terminates in an annular finger-receiving opening 244. Movement of the handle mechanism causes the opening and closing of the forceps 218.

A conductive wire lead extends the entire length of the tubular member through each of the plurality of wire-receiving tubular members 222a-222c. The first lead is operatively connected to a first conductive jaw 260 of the coagulating forceps 218 and to one of the leads 221 for connecting the jaw to the generator 10. The first jaw 260 has a slot (not shown) for receiving the cutting blade 220 therein.

A second lead is operatively connected to the second conductive jaw 264 of the coagulating forceps 218 and to another of the leads 221. The second jaw 264 has a slot (not shown) aligned with the slot on the first jaw 260 for receiving the blade 220 therein. A third lead is connected to the cutting blade 220, and also to one of the leads 221. In this way, the jaws 260 and 264, as well as the cutting blade 220, can all be energized by the generator.

A cutting instrument actuating lever 270 is pivotally attached to the handle 216 near its distal end, as shown in FIG. 19. The actuating lever 270, which extends into the longitudinal section 234 of the handle, contains a socket (not shown) for receiving the end of the cutting instrument actuating rod 232. Movement of the actuating lever 270 advances and retracts the blade actuating rod 232, and hence the cutting blade 220.

The instrument 12 is intended to be used in conjunction with a cannula, however, it is not limited to such use. In use, the instrument 12 will have its tubular member 208 inserted through the lumen of a cannula extending through a puncture formed in the abdominal wall. The surgeon views a surgical site via a laparoscope and locates the tissue such as the cystic duct which links the gall bladder and the common bile duct. The bipolar coagulating forceps jaws 260 and 264 are positioned about the cystic duct at the location to be coagulated and cut. The surgeon then pulls the moveable handle arm 242 towards the stationary arm 236, causing the wire guide sleeve 224 to extend beyond the distal end of the tubular member 208. This motion facilitates the closing of the coagulating forceps jaws 260 and 264 in that, as the wire guide sleeve 224 advances, it closes the forceps jaws 260 and 264 onto the tissue.

As the tissue is clamped, RF power generated by the electrosurgical generator 10 is applied which causes current to flow between electrode surfaces 262 and 268 on the jaws 260 and 264 to thereby heat and coagulate the tissue pinched between the two jaw electrodes. Simultaneously with the above operation, the generator 10 supplies RF power to the cutting blade 220. The actuating lever 270 of the handle 216 is pulled towards the moveable arm 242 of the handle 216. This causes the blade 220 to extend from the distal end of the tubular member 208, within the blade receiving slots formed in the jaws.

Once the tissue is cut, by the combination of the mechanical action of the cutting blade 220 and the RF power supplied thereto, the blade is retracted by removing pressure from the actuator lever 270. The forceps jaws 260 and 264 may be released by moving the handle arm 242 towards the lever 270 of the handle 216, which opens the jaws. The multi-phase nature of the RF power supplied from the generator 10 allows for the tissue to be simultaneously coagulated between the jaws 260 and 264, while being cut by the advancing cutting blade 220

FIGS. 20 to 25 show an alternative embodiment for the distal end of the instrument 12, where this time the cutting electrode 220 is in the form of an elongate rail, extending along the length of a conductive jaw member 264. The rail 220 is mounted on top of a ceramic insulator 317, such that it is insulated from the conductive tissue-contacting parts 380 and 381 of the jaw member 264. The rail 220 is typically 100 to 200 microns in width, and protrudes from the ceramic insulator 317 by a distance of approximately 50 microns. When the forceps assembly 218 is in its closed position, the rail 220 is received in a corresponding longitudinal recess 323 in the other conductive jaw member 260, as will now be described in further detail.

The recess 323 runs completely through the jaw member 260 from top to bottom, creating an opening therein. This recess divides the jaw member 260 into two further conductive tissue-contacting members 383 and 384. The tissue-contacting members 383 and 384 constitute sealing members for sealing against tissue gripped by the jaw member 260. A longitudinally-extending anvil 327 is received within the recess 323, the anvil 327 being formed of an insulating polymer material, and being aligned with the cutting electrode 220 in the jaw member 264. When the jaw members 260 and 264 are closed, the anvil 327 pushes the tissue 332 against the cutting electrode 220. The anvil 327 is spring mounted on its support member (not shown) such that it can move by at least 0.5 mm, preferably by at least 1 mm, and conceivably by as much as 2.5 mm when tissue is grasped between the two jaw members 260 and 264.

The operation of the cutting forceps instrument 12 will now be described. FIG. 20 shows the jaw members 260 and 264 in their rest position, closed but with no tissue grasped therebetween. The cutting electrode 220 pushes the anvil 327 upwardly against the support member (not shown).

Figure 23:
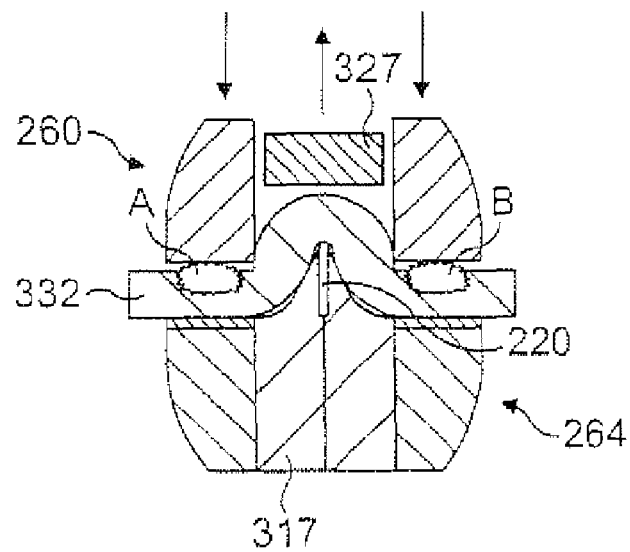

FIG. 21 shows the jaw members 260 and 264 in their open position, with tissue 332 therebetween. With the jaw members 260 and 264 in the open position, the anvil 327 is no longer pushed upwardly by the cutting electrode 220, and consequently assumes a position more level with the base or tissue-contacting surfaces of the jaw member 260. The jaw members 260 and 264 are then closed as shown in FIGS. 22 and 23, such that the tissue 332 is squeezed between the jaw members. The anvil 327 is pushed upwardly by the tissue 332 against the spring action of the support member, so as not to exert so great a force on the tissue as to squeeze the tissue against the cutting electrode 220 as it is gripped between the tissue-contacting members 380, 381, 383 and 384 of the jaw members 260 and 264.

Figure 24:
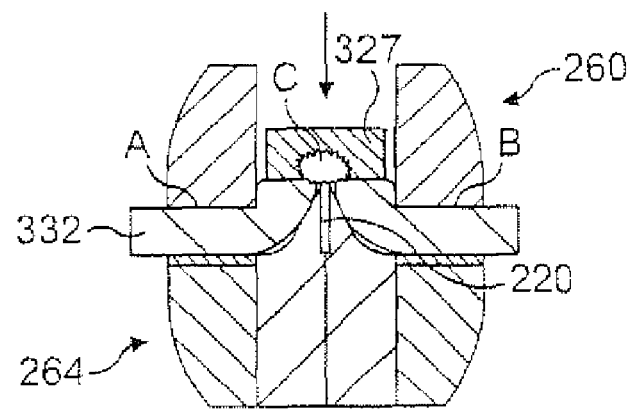
Figure 25:
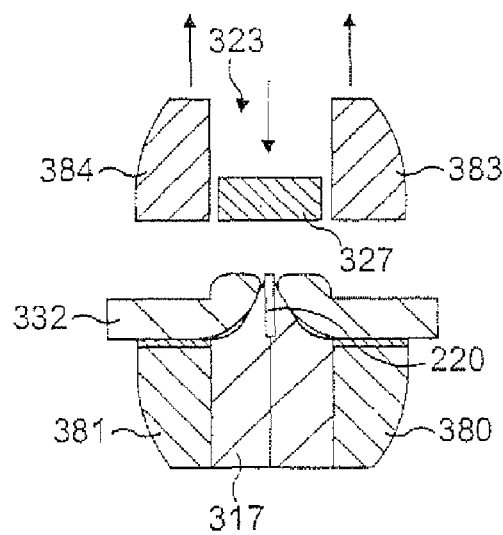

Typically, the pressure exerted on the tissue 332 by the tissue-contacting members 380, 381, 383 and 384 of the jaw members 260 and 264 in the sealing areas A and B, as depicted in FIG. 23, is between 0.5 and 1.0 MPa. When the jaw members 260 and 264 have been fully closed, the electrosurgical generator 10 is actuated to supply a coagulating RF signal between the jaw members. This coagulates the tissue 332 in the sealing areas A and B and the tissue may shrink in size due to this coagulating action. Simultaneously, or after a delay of about 1 second, a cutting RF signal is supplied between the cutting electrode 220 and the jaw members 260 and 264. This is shown in FIG. 24, during which time the spring movement of the anvil 327 exerts a force against the tissue 332 of typically between 0.08 and 0.25 N/mm. The cutting electrode 220 electrosurgically severs the tissue 232 in the cutting area C as shown in FIG. 24, the cutting area C lying between the sealing areas A and B, such that blood flow to the cutting area is prevented. The jaw members 260 and 264 can then be re-opened as shown in FIG. 25 to release the severed tissue 332.

As an alternative to the 1 second delay mentioned above, the generator 10 can measure the impedance of the tissue 332 grasped between the jaws 260 and 264, and monitor the change in this impedance as the coagulating RF signal is supplied therebetween. When the impedance rises to a level that indicates that sufficient coagulation has started to occur, the generator 10 may initiate the cutting RF signal, which is then supplied simultaneously with the continuing coagulating RF signal.

As has been described previously with reference to FIG. 18, it is possible with the multi-phase generator to vary the relative magnitudes of the cutting voltage output and coagulating voltage output. Therefore, as a further alternative to the 1 second delay described above, the generator operating sequence can begin with an output that is predominantly an RF coagulating output, and then change at some later time to an output that is predominantly an RF cutting output. This change can be at a preset time after the coagulating output has been initiated, or can be a gradual change over a short period of time. Either way, this ensures that the tissue is sufficiently coagulated before cutting is effected, while still providing a quicker overall process by the supply of cutting and coagulating signals simultaneously.

Figure 26:
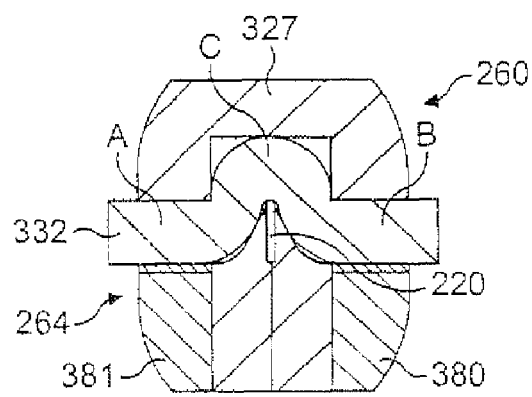
FIG. 26 is a schematic sectional view of a further alternative instrument suitable for use in the electrosurgical system of FIG. 19.

FIG. 26 shows an alternative embodiment in which the anvil 327 is integral with the remainder of the jaw member 260, and the tissue contacting members 380 & 381 are electrically isolated such that they can be connected to different outputs of the generator 10. Referring back to FIG. 7 or 13, cutting electrode 220 is connected to output 18-1 of the generator, tissue contacting member 380 is connected to output 18-2 of the generator, and tissue contacting member 381 is connected to output 18-3 of the generator. Jaw member 260 is connected to the output 18-4 of the generator, which is the neutral output line, as previously described. When tissue is grasped between the jaw members as shown in FIG. 26, the tissue is coagulated in area A between tissue contacting member 381 and jaw member 260, and also coagulated in area B between tissue contacting member 380 and jaw member 260. There may also be some slight coagulating effect in the tissue due to currents passed between tissue contacting members 380 and 381, or between each of the tissue contacting members 380 and 381 and the cutting electrode 220. However, there will also be a cutting effect on the tissue in area C caused by the higher current flowing between cutting electrode 220 and the jaw member 260. As before, these coagulating and cutting effects can be initiated simultaneously, or after a period of pure coagulation (or at least reduced cutting). Alternatively, and also as described previously, the proportion of cutting in a blended signal can be steadily increased, or suddenly increased after a period of predominantly coagulative signals.

Whichever arrangement is employed, by supplying the cutting and coagulating signals simultaneously, as is possible with the multi-phase generator described herein, the duration of the process to coagulate and cut the tissue 332 can be minimized, while ensuring that sufficient coagulation occurs before the tissue is severed.

While the invention has been described in connection with what is presently considered to be the most practice and preferred embodiments, it is to be understood that the invention is not to be limited to the disclosed embodiments, but on the contrary, is intended to cover various modifications and equivalent arrangements included within the spirit and scope of the appended claims.

What is claimed is:

1. An electrosurgical system comprising an electrosurgical generator for generating radio frequency (RF) power at a generator operating frequency and an electrosurgical instrument coupled to the generator, wherein the generator comprises a multiple-phase RF output stage having at least three outputs for coupling to respective electrodes of the electrosurgical instrument for delivering RF power to the electrodes, wherein the electrosurgical instrument is a forceps instrument comprising first and second jaws coupled to first and second generator outputs, the first and second jaws being adapted to coagulate tissue grasped therebetween, the forceps instrument also including a cutting electrode coupled to a third generator output, the cutting electrode being adapted to cut tissue grasped between the jaws, and wherein the configuration of the output stage of the generator is such that respective RF output voltage waveforms are simultaneously delivered across each pair of said three outputs at the operating frequency, each such waveform being phase-displaced with respect to the waveforms delivered across the respective other pairs of the three outputs, such that the forceps instrument is capable of the simultaneous coagulation and cutting of tissue.

2. A system according to claim 1, wherein the generator is adapted to supply an RF coagulating voltage between the first and second generator outputs, and an RF cutting voltage between the third generator output and one or both of the first and second generator outputs.

3. A system according to claim 2, wherein the generator is adapted to supply the RF output voltage waveforms in a two stage profile, with a first, coagulation stage during which the generator supplies primarily an RF coagulating voltage, said coagulating voltage being supplied to the first and second jaws, followed by a second, blended stage during which the generator supplies an RF cutting voltage to the cutting electrode simultaneously with the RF coagulating voltage continuing to be supplied to the first and second jaws.

4. A system according to claim 3, wherein the transition from the first stage to the second stage takes place after a predetermined time period has elapsed.

5. A system according to claim 3, wherein the transition from the first stage to the second stage takes place after a measured tissue parameter reaches a predetermined threshold value.

6. A system according to claim 5, wherein the measured parameter is the impedance of the tissue.

7. A system according to claim 2, wherein the generator is adapted to vary over time the magnitudes of the RF cutting voltage and the RF coagulating voltage with respect to one another.

8. A system according to claim 7, wherein the generator is adapted to change from a first stage in which the RF coagulating voltage predominates, to a second stage in which the RF cutting voltage predominates.

9. A system according to claim 8, wherein the transition from the first stage to the second stage takes place at a predetermined time.

10. A system according to claim 8, wherein the transition from the first stage to the second stage takes place gradually.

11. A system according to claim 1, wherein the cutting electrode is in the form of a longitudinally moveable blade.

12. A system according to claim 1, wherein the cutting electrode is in the form of a stationary member located on one of the jaws.

* * * * *